US008686368B2

(12) United States Patent
Tybinkowski et al.

(10) Patent No.: US 8,686,368 B2
(45) Date of Patent: Apr. 1, 2014

(54) HIGH RESOLUTION SINGLE PHOTON EMISSION COMPUTED TOMOGRAPHY (SPECT) SYSTEM

(75) Inventors: Andrew Tybinkowski, Boxford, MA (US); Eric Bailey, Hampton, NH (US); Lidia Nemirovsky, Salem, MA (US); Daniel Allis, Lynn, MA (US)

(73) Assignee: NeuroLogica Corp., Danvers, MA (US)

( * ) Notice: Subject to any disclaimer, the term of this patent is extended or adjusted under 35 U.S.C. 154(b) by 93 days.

(21) Appl. No.: 13/154,195

(22) Filed: Jun. 6, 2011

(65) Prior Publication Data

US 2011/0303851 A1    Dec. 15, 2011

Related U.S. Application Data

(60) Provisional application No. 61/351,750, filed on Jun. 4, 2010.

(51) Int. Cl.
*G01T 1/166* (2006.01)
(52) U.S. Cl.
USPC ................................ 250/363.05; 250/363.04
(58) Field of Classification Search
USPC ......................................... 250/363.04, 363.05
See application file for complete search history.

(56) References Cited

U.S. PATENT DOCUMENTS

| | | | | |
|---|---|---|---|---|
| 4,849,638 | A * | 7/1989 | Hawman | 250/363.02 |
| 5,107,121 | A * | 4/1992 | Lim et al. | 250/363.05 |
| 5,338,936 | A * | 8/1994 | Gullberg et al. | 250/363.04 |
| 5,486,700 | A * | 1/1996 | Silberklang et al. | 250/363.04 |
| 5,866,906 | A * | 2/1999 | Jensen | 250/363.05 |
| 7,175,347 | B2 | 2/2007 | Tybinkowski et al. | |
| 2002/0143249 | A1* | 10/2002 | Tornai et al. | 600/425 |
| 2007/0086563 | A1* | 4/2007 | Bruder | 378/8 |
| 2008/0084961 | A1* | 4/2008 | Keppel et al. | 378/37 |
| 2010/0128851 | A1* | 5/2010 | Bailey et al. | 378/198 |

FOREIGN PATENT DOCUMENTS

EP    0 480 537    4/1992

* cited by examiner

*Primary Examiner* — David Porta
*Assistant Examiner* — Abra Fein
(74) *Attorney, Agent, or Firm* — Pandiscio & Pandiscio

(57) ABSTRACT

A high resolution single photon emission computed tomography (SPECT) imaging system comprising:
a rotating ring for surrounding anatomy which is to be imaged;
at least one camera mount movably mounted to the rotating ring so that the camera mount can be moved radially relative to the axis of rotation of the rotating ring; and
at least one gamma camera carried on the at least one camera mount, wherein the at least one gamma camera is focused on a single SPECT focal point;
whereby, when the rotating ring is rotated about the anatomy which is to be imaged and the at least one camera mount is moved radially on the rotating ring, the single SPECT focal point of the at least one gamma camera carried by a camera mount follows a spiral pattern through the anatomy, whereby to produce a scan of the anatomy.

22 Claims, 40 Drawing Sheets

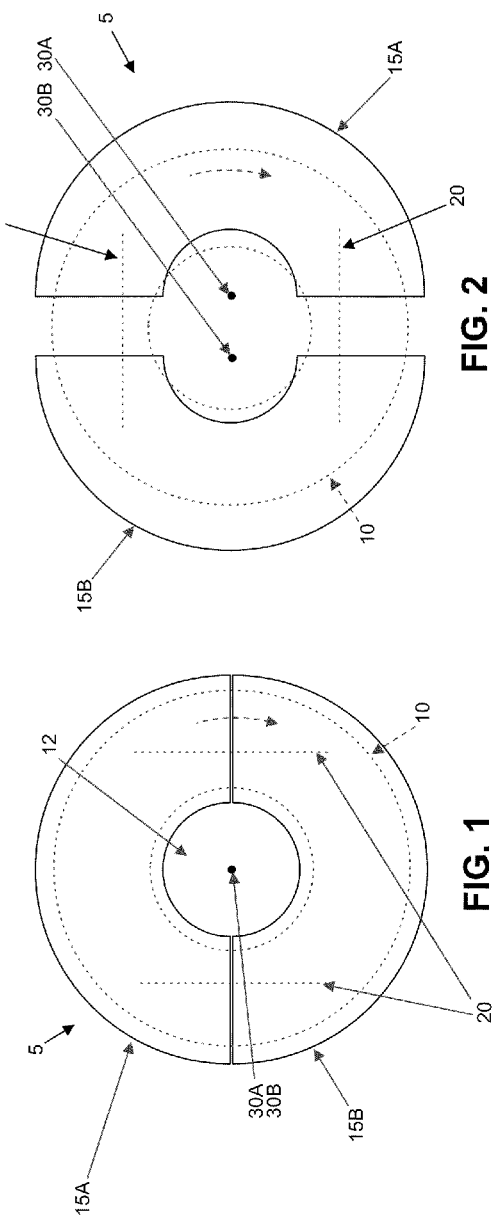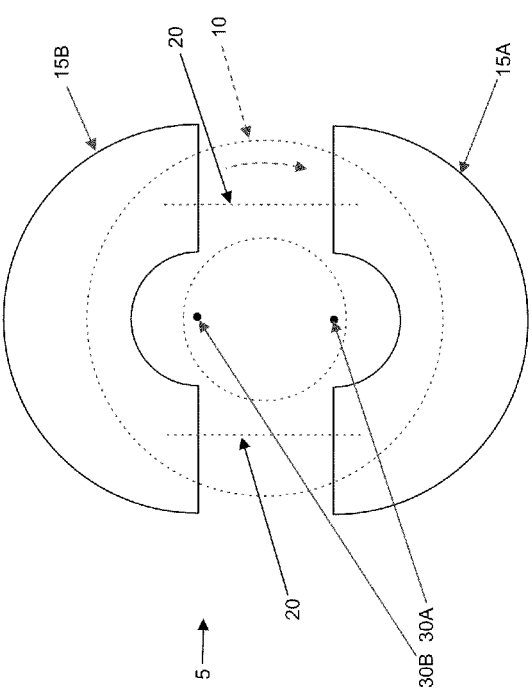

US 8,686,368 B2

HIGH RESOLUTION SINGLE PHOTON EMISSION COMPUTED TOMOGRAPHY (SPECT) SYSTEM

REFERENCE TO PENDING PRIOR PATENT APPLICATION

This patent application claims benefit of pending prior U.S. Provisional Patent Application Ser. No. 61/351,750, filed Jun. 4, 2010 by Andrew P. Tybinkowski et al. for HIGH RESOLUTION SINGLE PHOTON EMISSION COMPUTED TOMOGRAPHY (SPECT) SYSTEM which patent application is hereby incorporated herein by reference.

FIELD OF THE INVENTION

This invention relates to anatomical imaging systems in general, and more particularly to single photon emission computed tomography (SPECT) systems.

BACKGROUND OF THE INVENTION

Various types of anatomical imaging systems are well known in the art.

By way of example but not limitation, X-ray imaging systems comprise an X-ray source and an X-ray detector. The X-ray source is disposed on one side of the anatomy which is to be imaged, and the X-ray detector is disposed on the other side of the anatomy which is to be imaged. The X-ray detector captures the X-rays which pass through the anatomy, thereby forming a 2D image of the anatomy. Such 2D X-ray imaging systems are now in widespread use in hospitals, surgical centers, dental offices, etc.

By acquiring multiple 2D images from multiple angles of view, and subsequently assembling the data from those multiple 2D images using computed tomography (CT) techniques, 3D images of the anatomy can be produced. Such CT imaging systems are now in widespread use in hospitals, surgical centers and the like.

Numerous other imaging systems are well known in the art. By way of example but not limitation, ultrasound imaging systems and magnetic resonance imaging (MRI) systems are two other types of imaging systems which are now in widespread use around the world.

Another type of imaging system, and the one to which the present invention is directed, relies on scintigraphy, i.e., where radioisotopes are positioned internally within the body, and then a camera is used to capture and form an image of the radiation emitted by the radioisotopes. These scintigraphy systems may be relatively simple 2D systems or they may employ computed tomography (CT) techniques so as to produce 3D images of the anatomy.

One well known type of scintigraphy system is the single photon emission computed tomography (SPECT) system, where one or more moving cameras detect gamma radiation emitted by radioisotopes positioned within the body so as to produce multiple 2D images from multiple angles of view, and then computed tomography (CT) techniques are used to assemble the acquired 2D images into a 3D image.

Another well known type of scintigraphy system is the positron emission tomography (PET) system. This imaging system uses a radioisotope tracer, which emits positrons which then annihilate adjacent electrons, causing gamma photons to be emitted in opposite directions—these gamma photons are detected by the system so as to produce multiple 2D images from multiple angles of view, and then these multiple 2D images are assembled, using computed tomography (CT) techniques, into 3D images.

In general, PET imaging systems have a higher resolution than SPECT imaging systems. However, SPECT imaging systems are generally significantly less expensive to build and operate than PET imaging systems—this is because SPECT imaging systems are generally able to use longer-lived, and more easily-obtainable, radioisotopes than PET imaging systems, among other things.

Accordingly, there is currently a need for a new and improved SPECT imaging system which provides increased resolution compared to current SPECT imaging systems.

In addition to the foregoing, in prior art SPECT imaging systems, multiple gamma cameras have generally been used to acquire the multiple 2D images from multiple angles of view. However, in prior art SPECT systems, complex electromechanical systems have generally been required in order to control the movement of the multiple gamma cameras. The use of multiple gamma cameras, and their complex electromechanical control systems, significantly increases the cost to build and maintain such SPECT imaging systems.

Accordingly, there is a need for a new and improved SPECT imaging system which utilizes a simplified construction.

SUMMARY OF THE INVENTION

These and other objects of the present invention are addressed by a novel high resolution single photon emission computed tomography (SPECT) system which provides high resolution scanning while employing a simplified construction. The novel SPECT system of the present invention generally comprises a rotating ring which surrounds the anatomy which is to be imaged. At least one camera mount is movably mounted to the rotating ring so that the camera mount can be moved radially relative to the rotating ring (i.e., so that the camera mount can be moved inwardly or outwardly relative to the axis of rotation of the rotating ring). The camera mount carries a plurality of gamma cameras thereon, with the plurality of gamma cameras on that camera mount all being focused on a single SPECT focal point. As a result of the foregoing construction, as the rotating ring is rotated about the patient and the camera mount is moved radially on the rotating ring, the single SPECT focal point of the multiple gamma cameras carried by that camera mount follows a spiral pattern through the anatomy. As a result, the anatomy traversed by the single SPECT focal point is scanned by the SPECT imaging system so as to produce a scan of the anatomy. While such scanning is occurring, the anatomy and/or the rotating ring are preferably moved longitudinally relative to one another, in the manner of a CT or MRI machine, so as to produce volume scanning of the anatomy. In this way, a 3D image of the patient's anatomy can be produced.

In one preferred form of the invention, two camera mounts are provided on the rotating ring, with the two camera mounts being disposed diametrically opposed to one another on the rotating ring. With this construction, each of the two SPECT focal points follows a spiral pattern through the anatomy, with the two SPECT focal points being diametrically opposed to one another as they follow their respective spiral paths. Preferably the imaging system is constructed so that the two SPECT focal points can be superimposed on one another when their respective camera mounts are appropriately positioned on the rotating ring.

In another preferred form of the invention, just one camera mount is provided on the rotating ring, so that just one SPECT focal point traverses the anatomy.

And in another preferred form of the invention, three or more camera mounts are provided, so that three or more SPECT focal points traverse the anatomy.

In another preferred form of the invention, there is provided a high resolution single photon emission computed tomography (SPECT) imaging system comprising:

a rotating ring for surrounding anatomy which is to be imaged;

at least one camera mount movably mounted to the rotating ring so that the camera mount can be moved radially relative to the axis of rotation of the rotating ring; and at least one gamma camera carried on the at least one camera mount, wherein the at least one gamma camera is focused on a single SPECT focal point;

whereby, when the rotating ring is rotated about the anatomy which is to be imaged and the at least one camera mount is moved radially on the rotating ring, the single SPECT focal point of the at least one gamma camera carried by a camera mount follows a spiral pattern through the anatomy, whereby to produce a scan of the anatomy.

In another preferred form of the invention, there is provided a method for imaging anatomy, the method comprising:

providing a high resolution single photon emission computed tomography (SPECT) imaging system comprising:
  a rotating ring for surrounding anatomy which is to be imaged;
  at least one camera mount movably mounted to the rotating ring so that the camera mount can be moved radially relative to the axis of rotation of the rotating ring; and
  at least one gamma camera carried on the at least one camera mount, wherein the at least one gamma camera is focused on a single SPECT focal point; and rotating the rotating ring about the anatomy which is to be imaged and moving the at least one camera mount radially on the rotating ring, so that the single SPECT focal point of the at least one gamma camera carried by a camera mount follows a spiral pattern through the anatomy, whereby to produce a scan of the anatomy.

In another preferred form of the invention, there is provided a method for imaging anatomy, the method comprising:

providing at least one camera focused on a focal point; and simultaneously moving, circumferentially and radially, the at least one camera relative to the anatomy so that the focal point follows a spiral pattern through the anatomy, whereby to produce a scan of the anatomy.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1-4 are schematic views of a SPECT imaging system formed in accordance with the present invention, wherein the SPECT imaging system comprises a rotating ring and two camera mounts diametrically opposed on the rotating ring so that two SPECT focal points traverse the anatomy;

DETAILED DESCRIPTION OF THE PREFERRED EMBODIMENTS

The present invention comprises a novel high resolution single photon emission computed tomography (SPECT) system which provides high resolution scanning of anatomy while employing a simplified construction.

Figure 4:
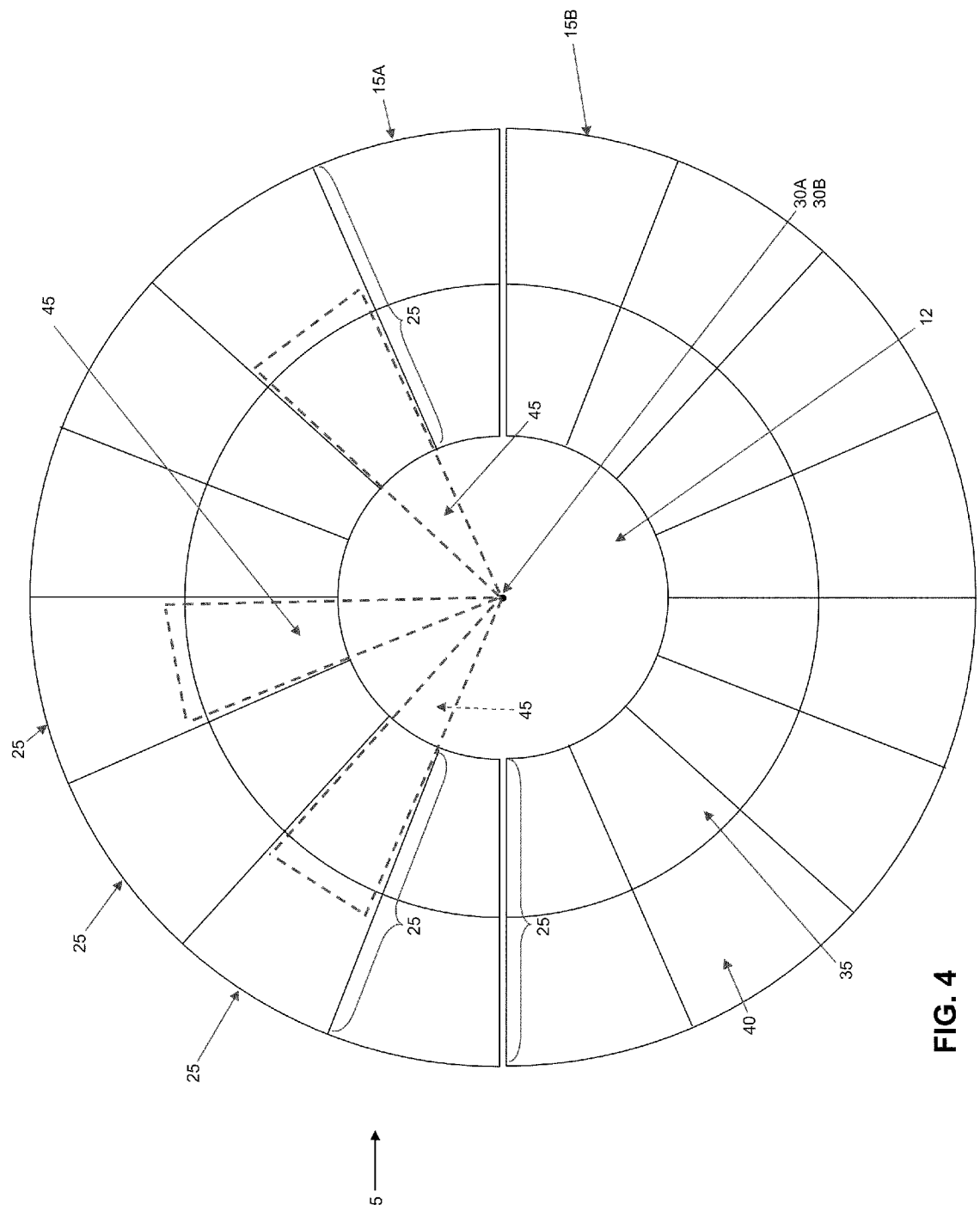
Figure 5:
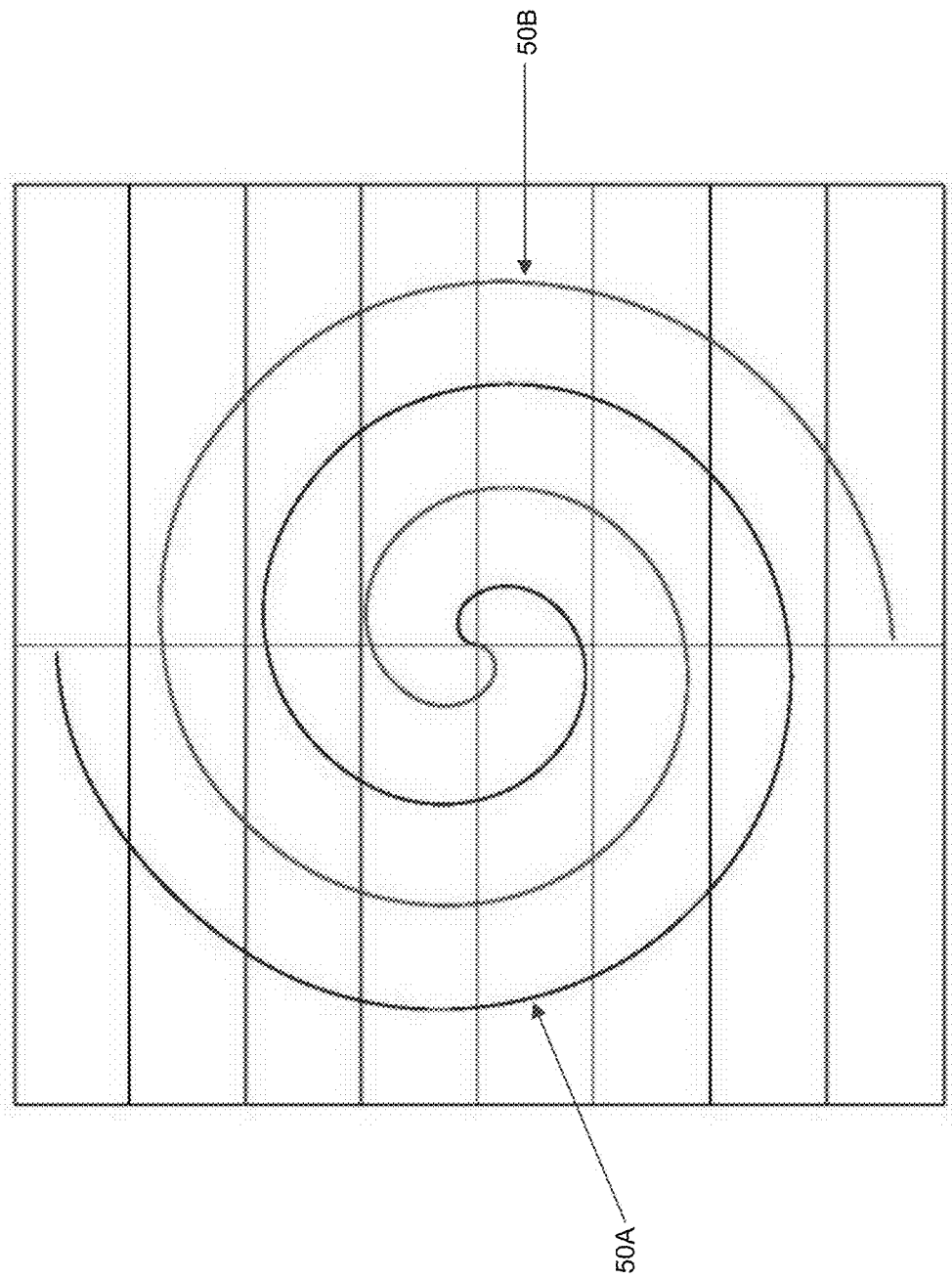
FIG. 5 is a schematic view showing the two spiral paths that are followed by the two SPECT focal points provided by the SPECT imaging system of FIGS. 1-4.
Figure 6:
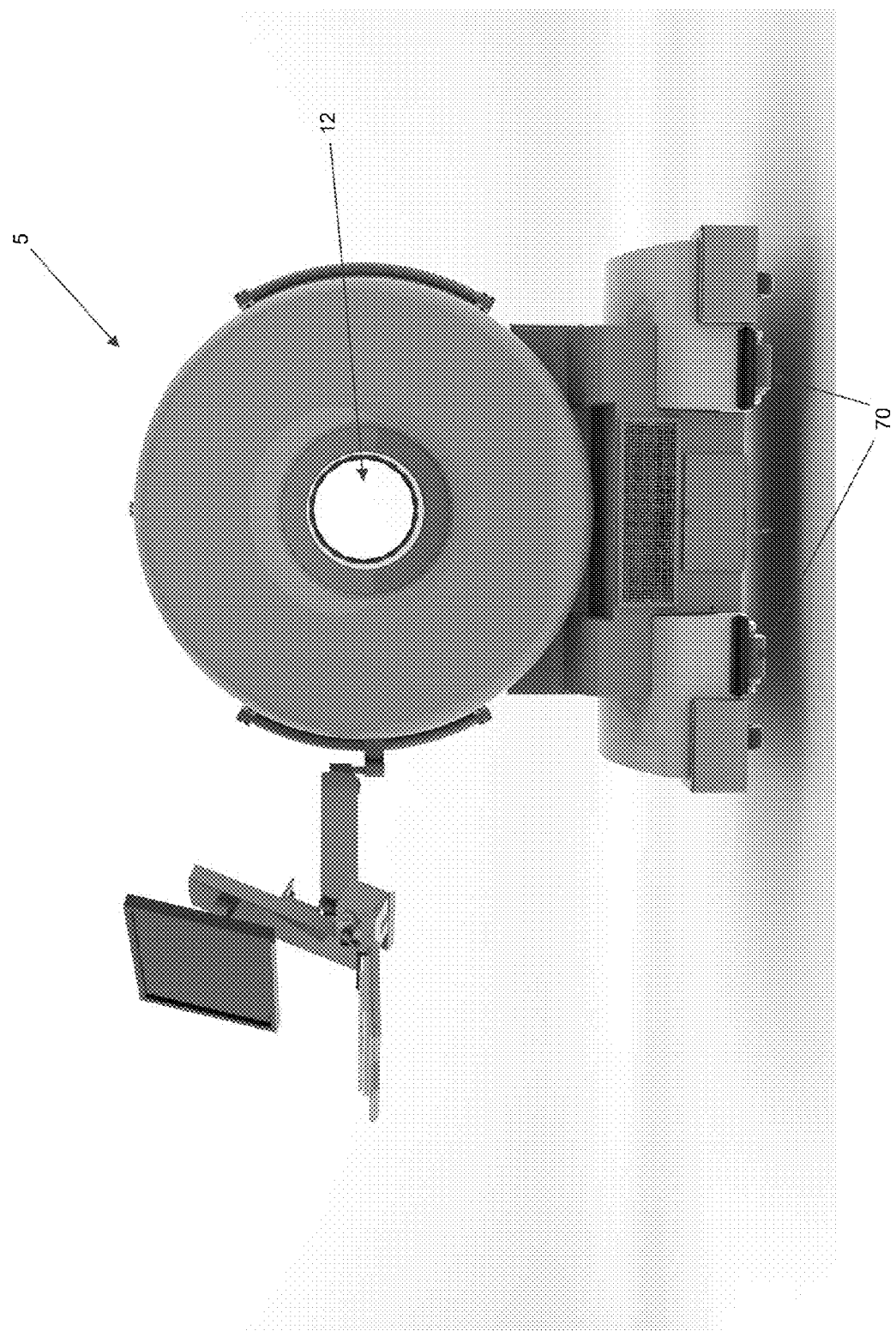
FIGS. 6-17 are schematic views showing selected aspects of a SPECT imaging system formed in accordance with the present invention, wherein the SPECT imaging system is adapted to move relative to the anatomy of the patient during scanning so as to produce volume scanning of the anatomy, e.g., in a manner analogous to that of the CT scanner disclosed in U.S. Pat. No. 7,175,347, which patent is hereby incorporated herein by reference.
Figure 7:
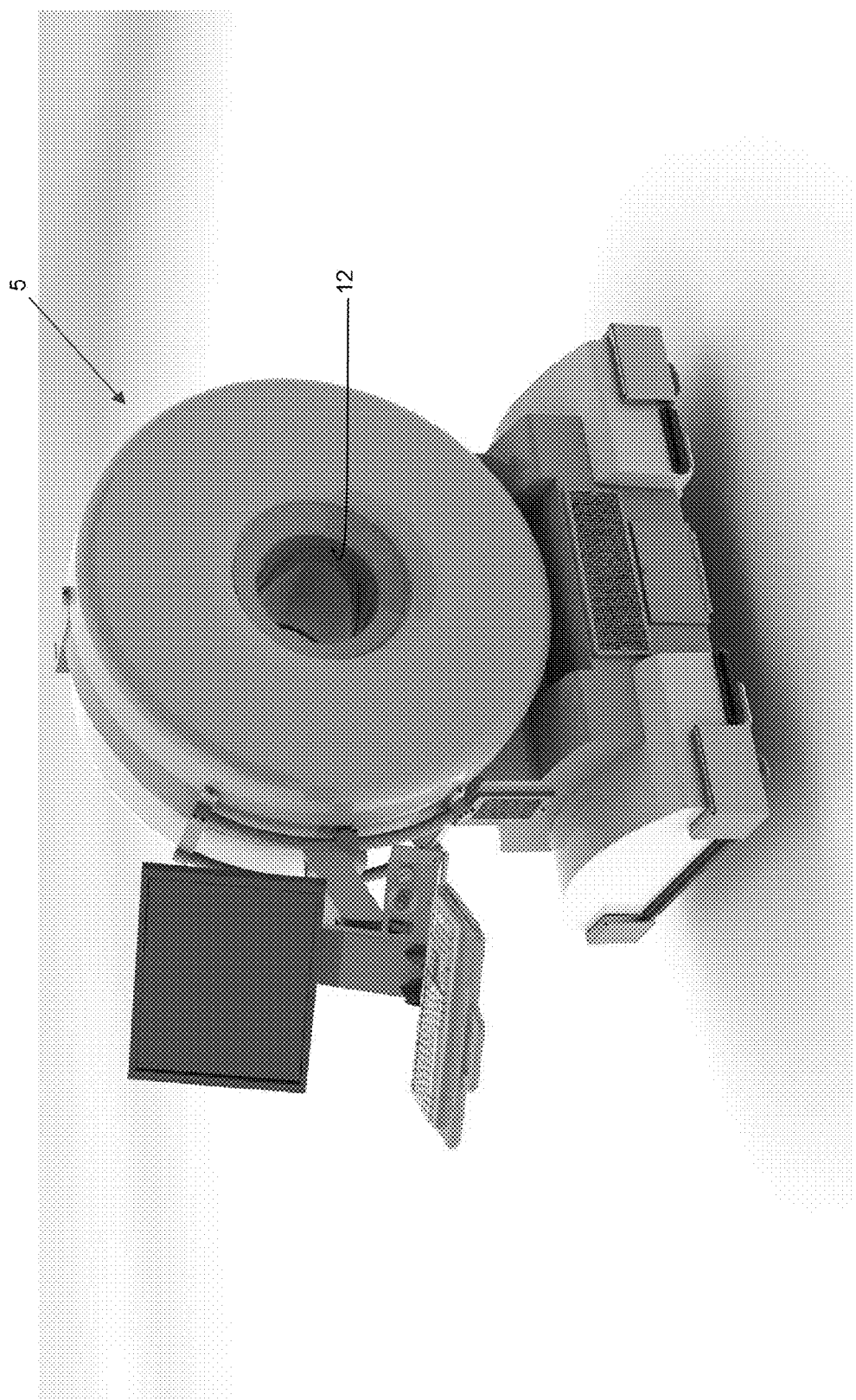
Figure 8:
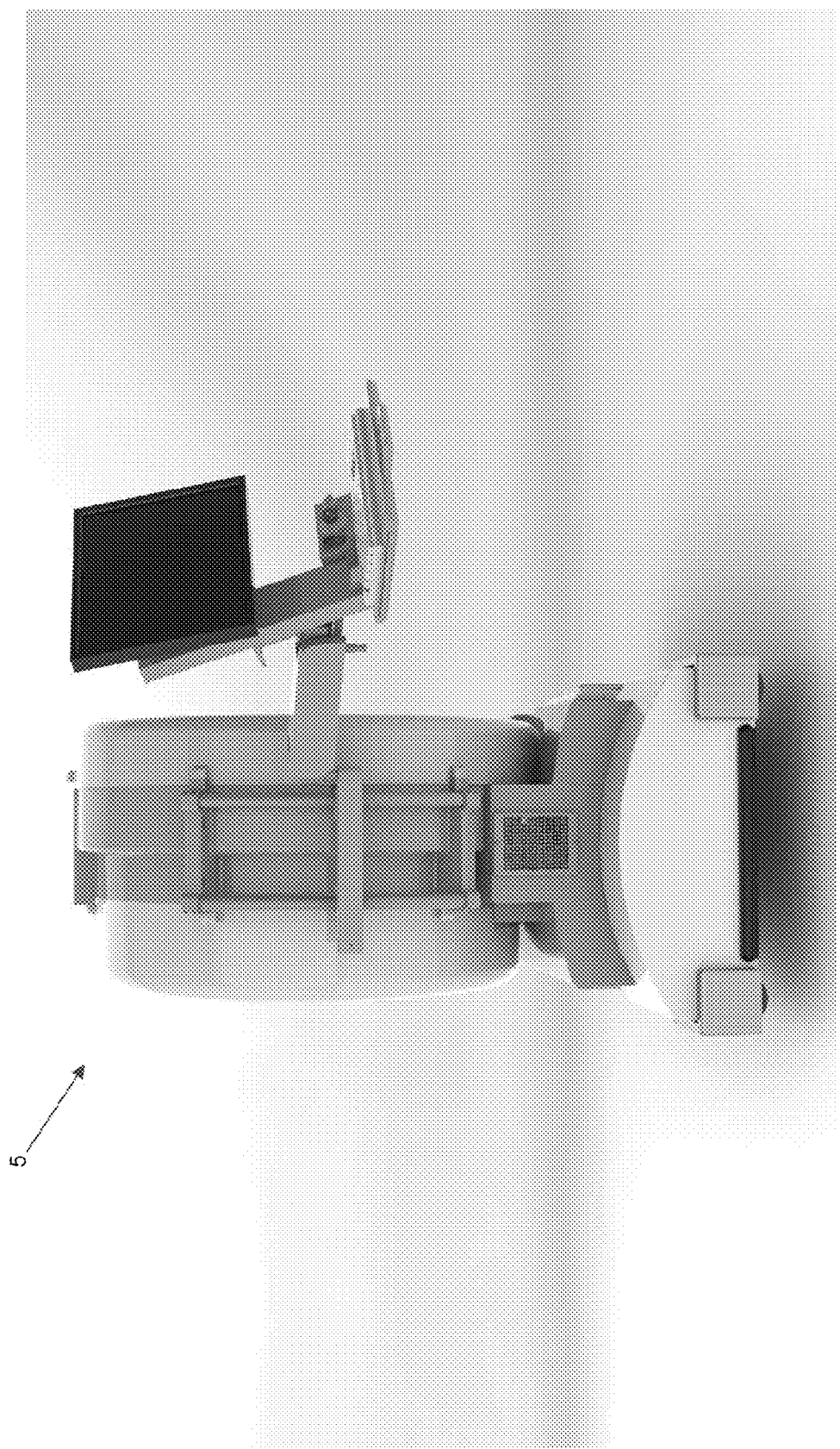
Figure 9:
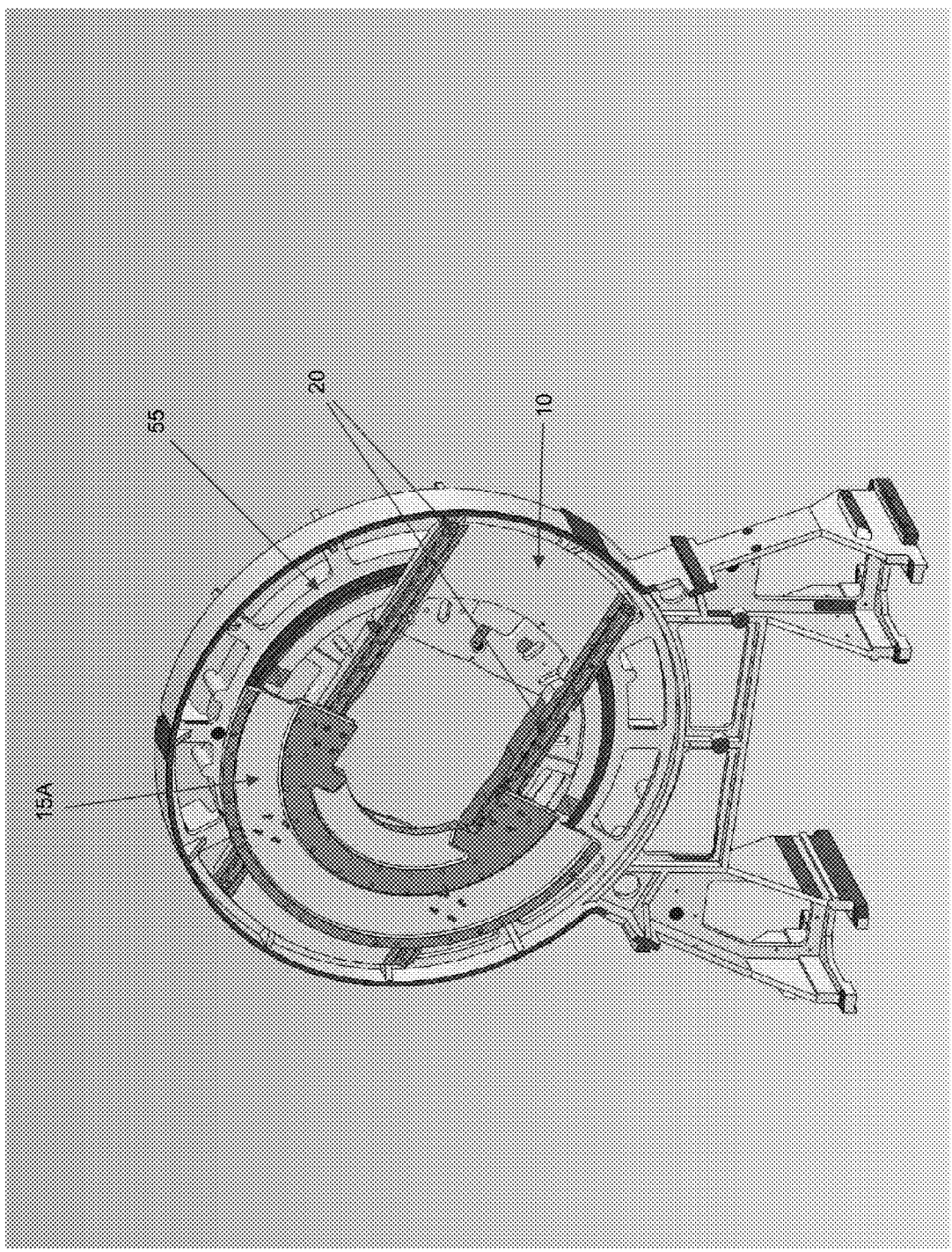
Figure 10:
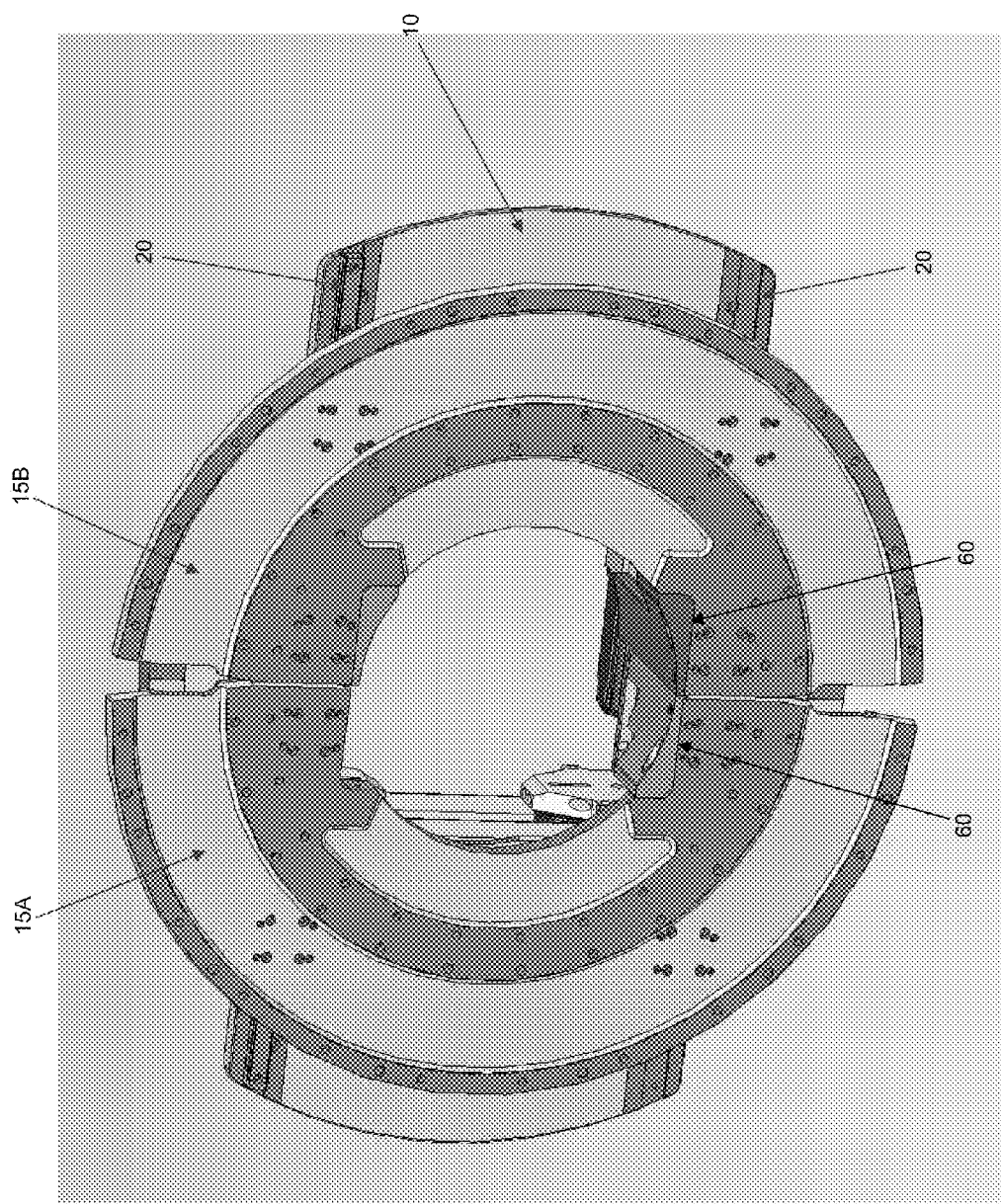
Figure 11:
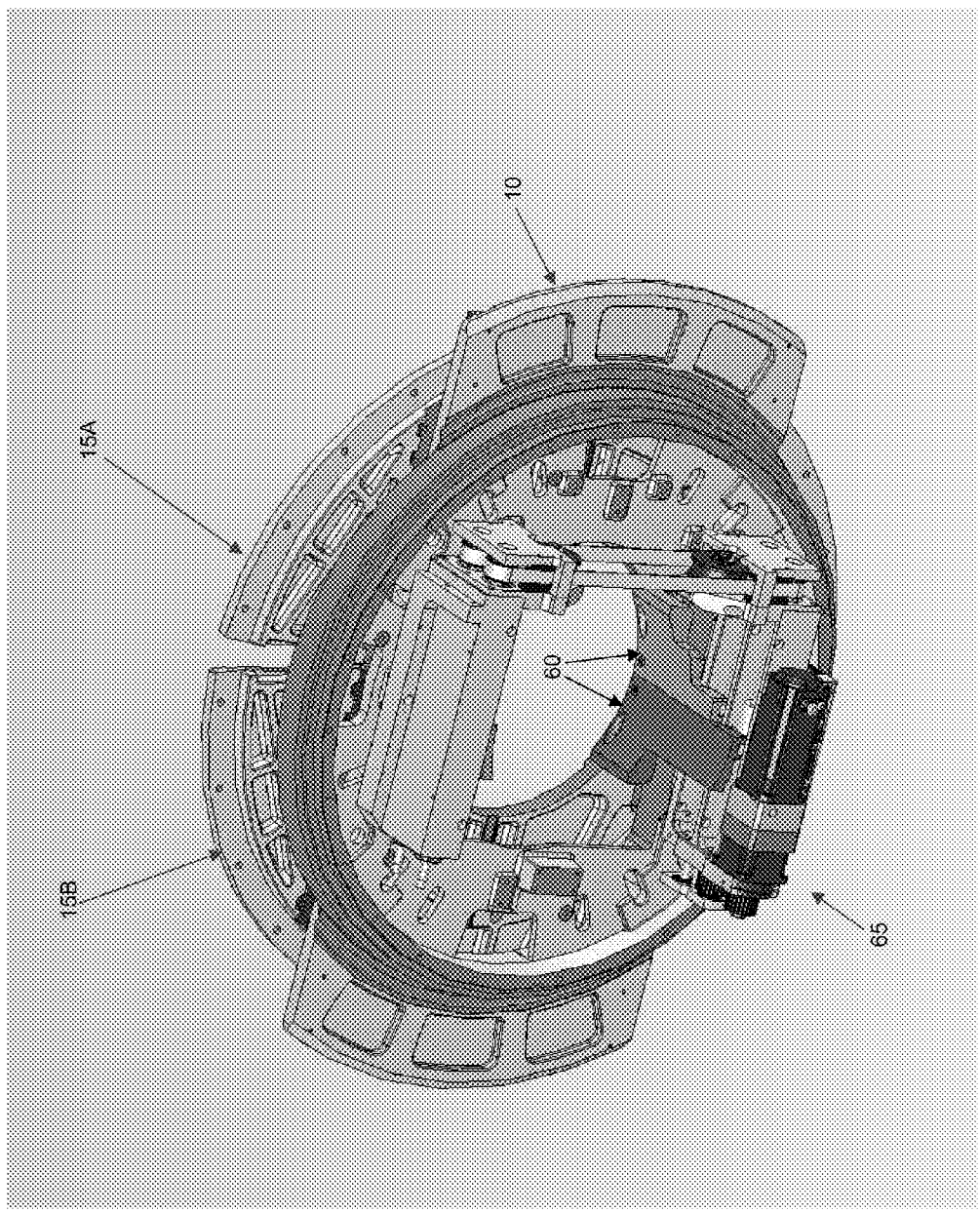
Figure 12:
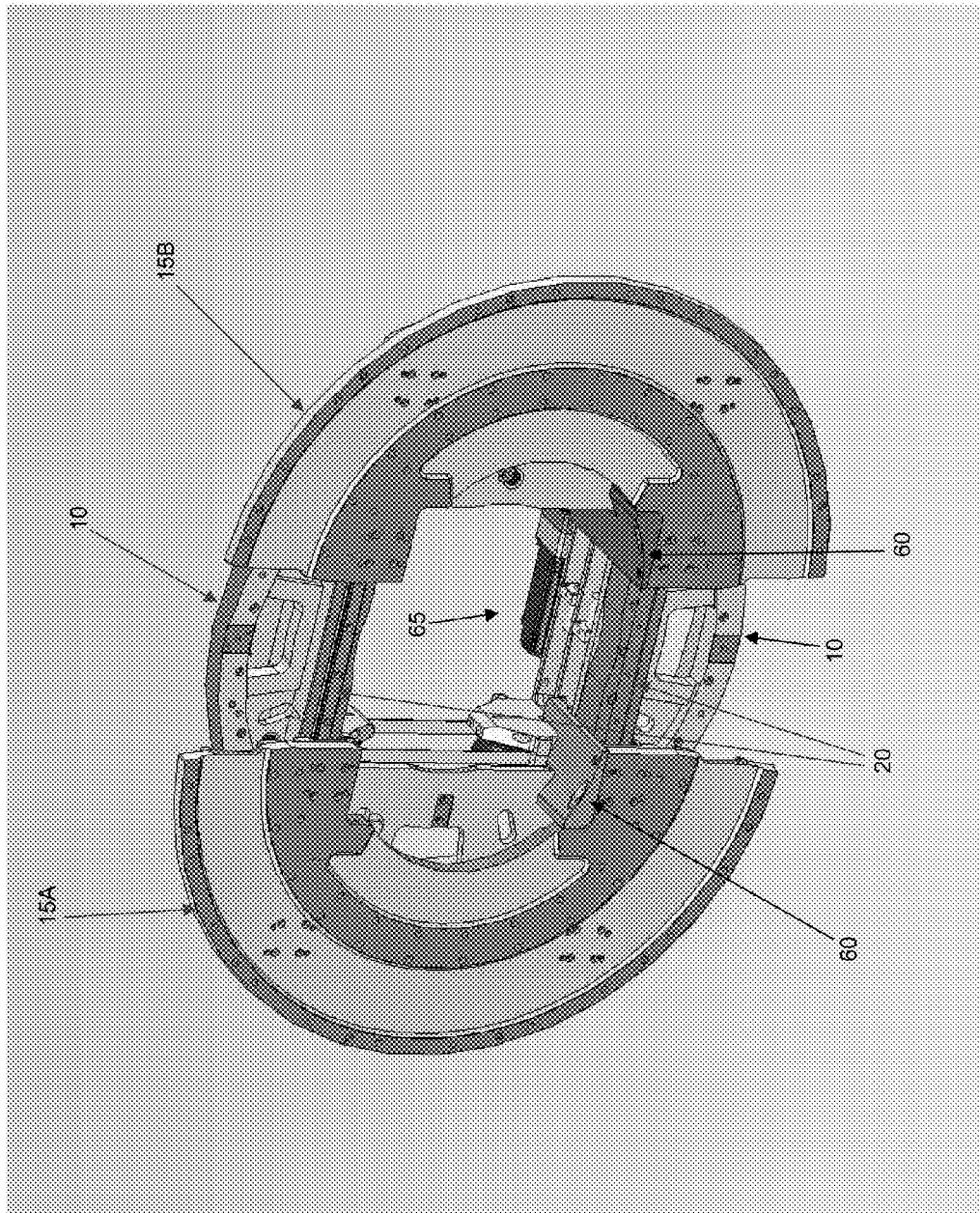
Figure 13:
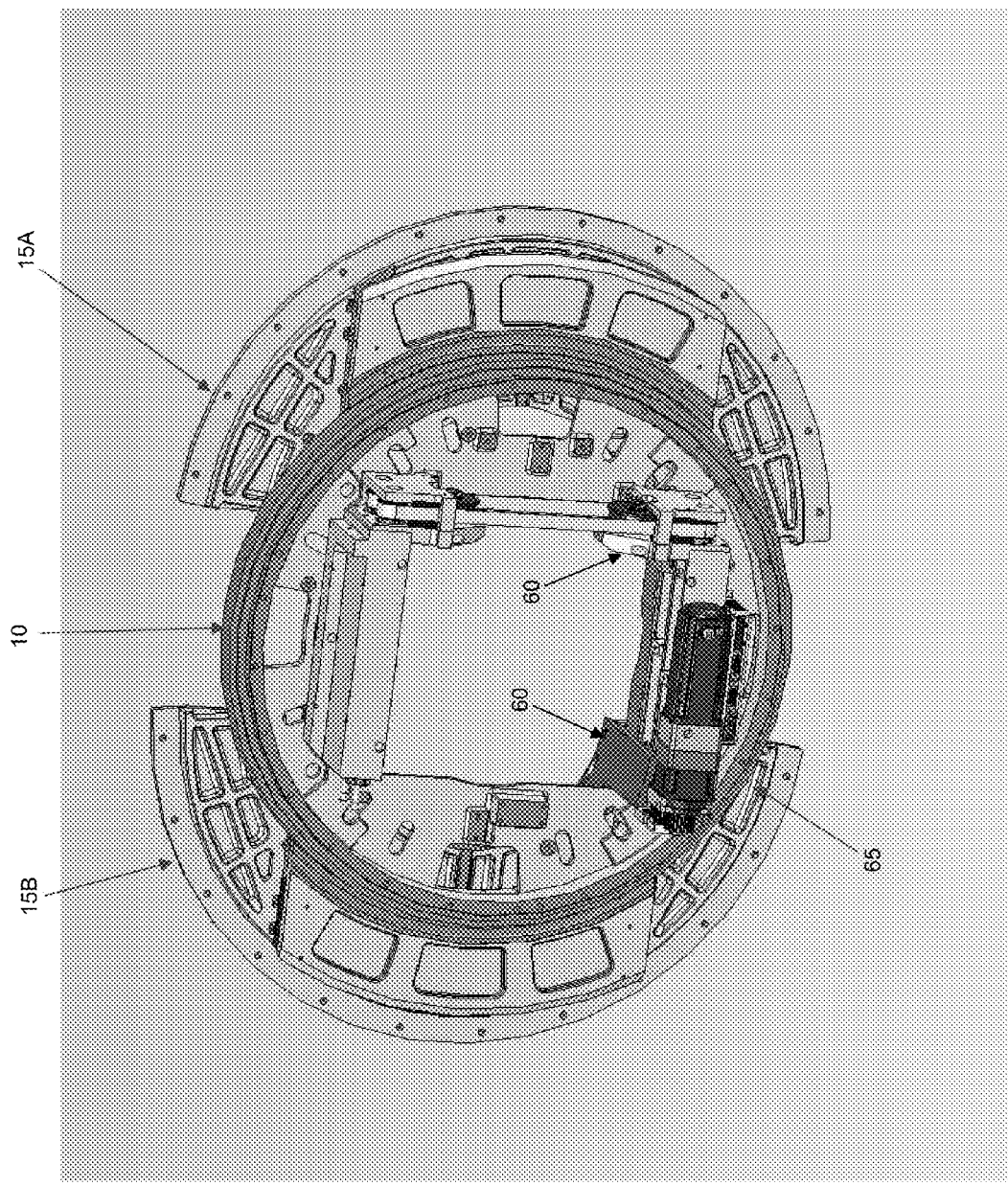
Figure 14:
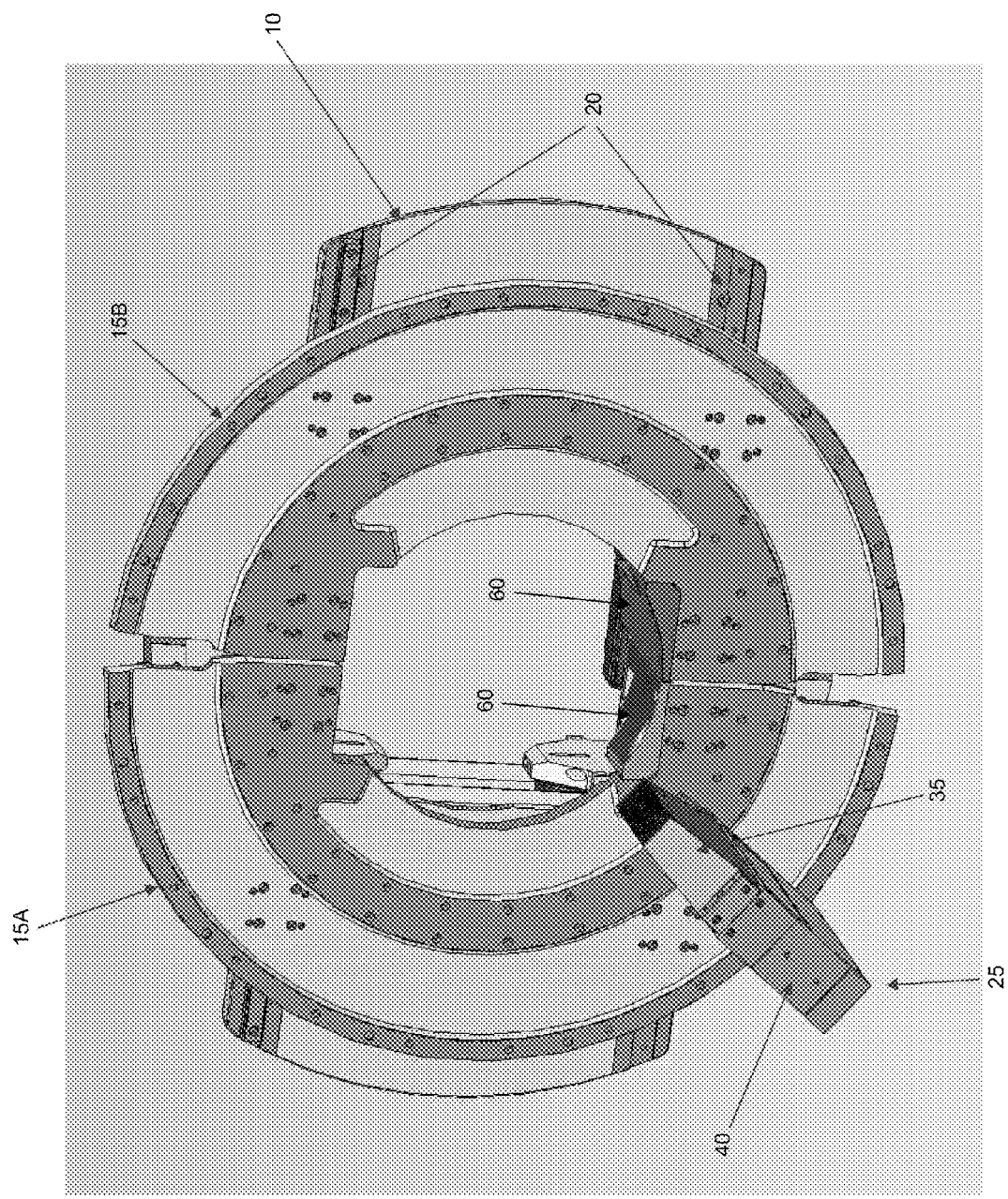
Figure 15:
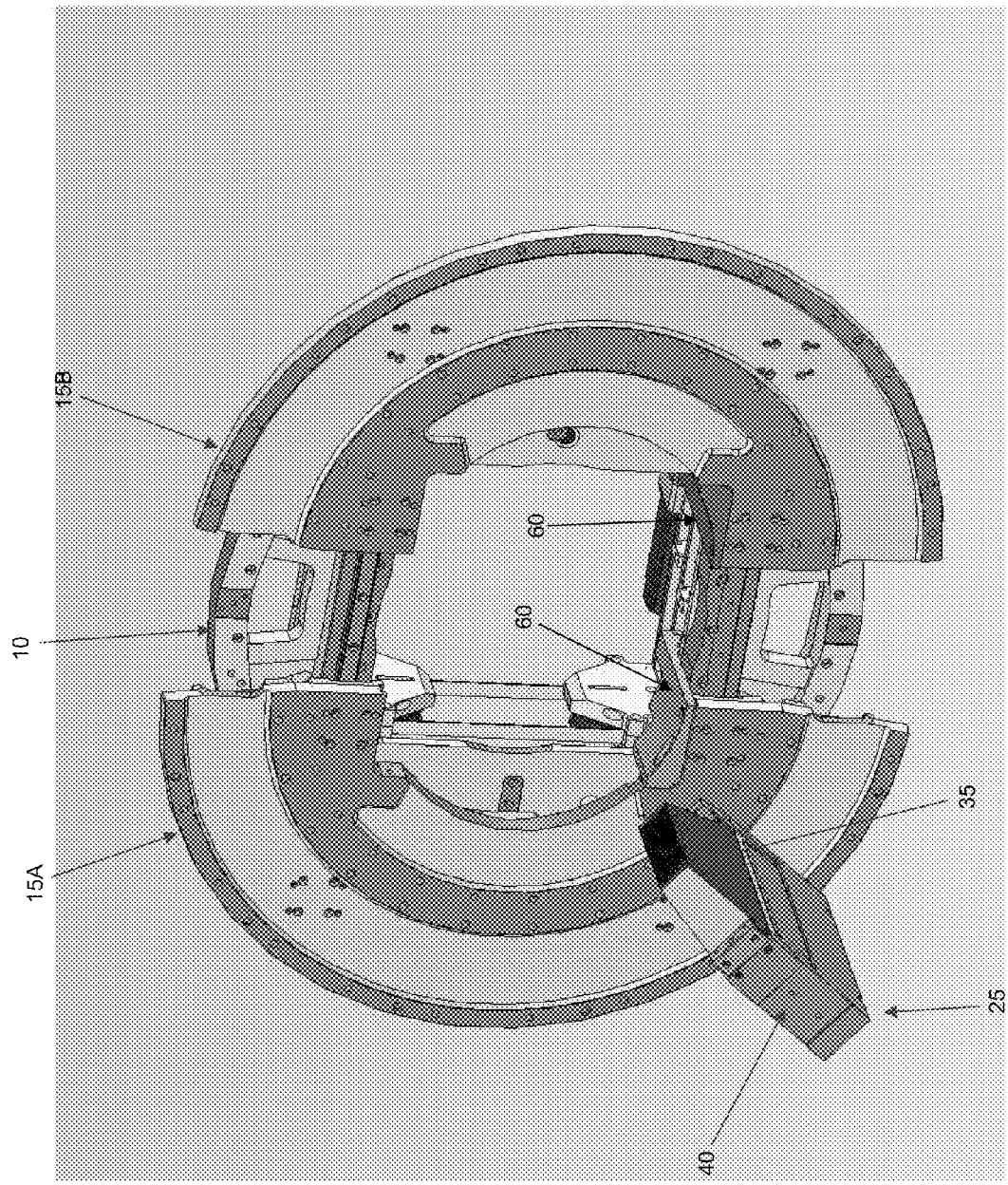
Figure 16:
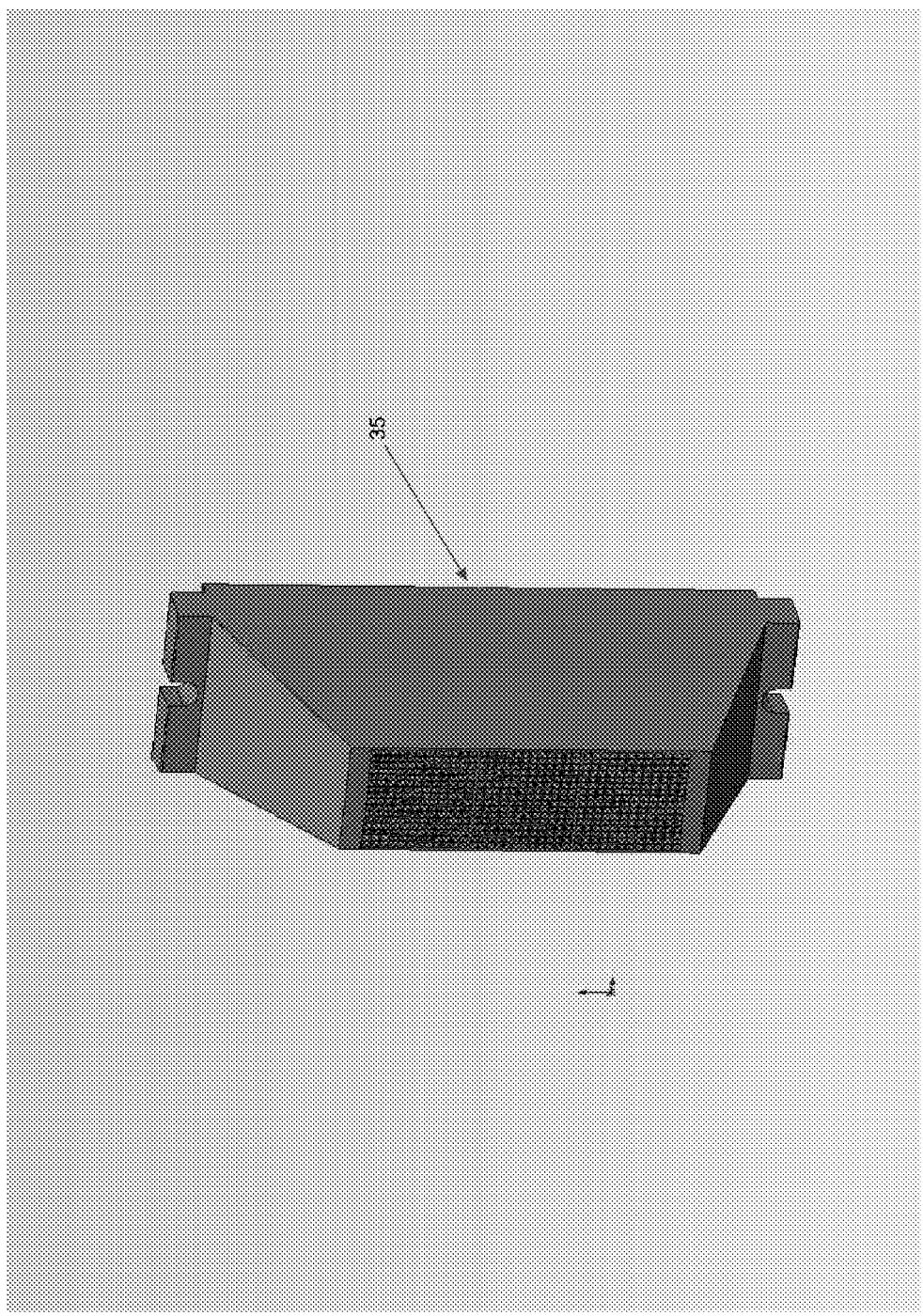
Figure 17:
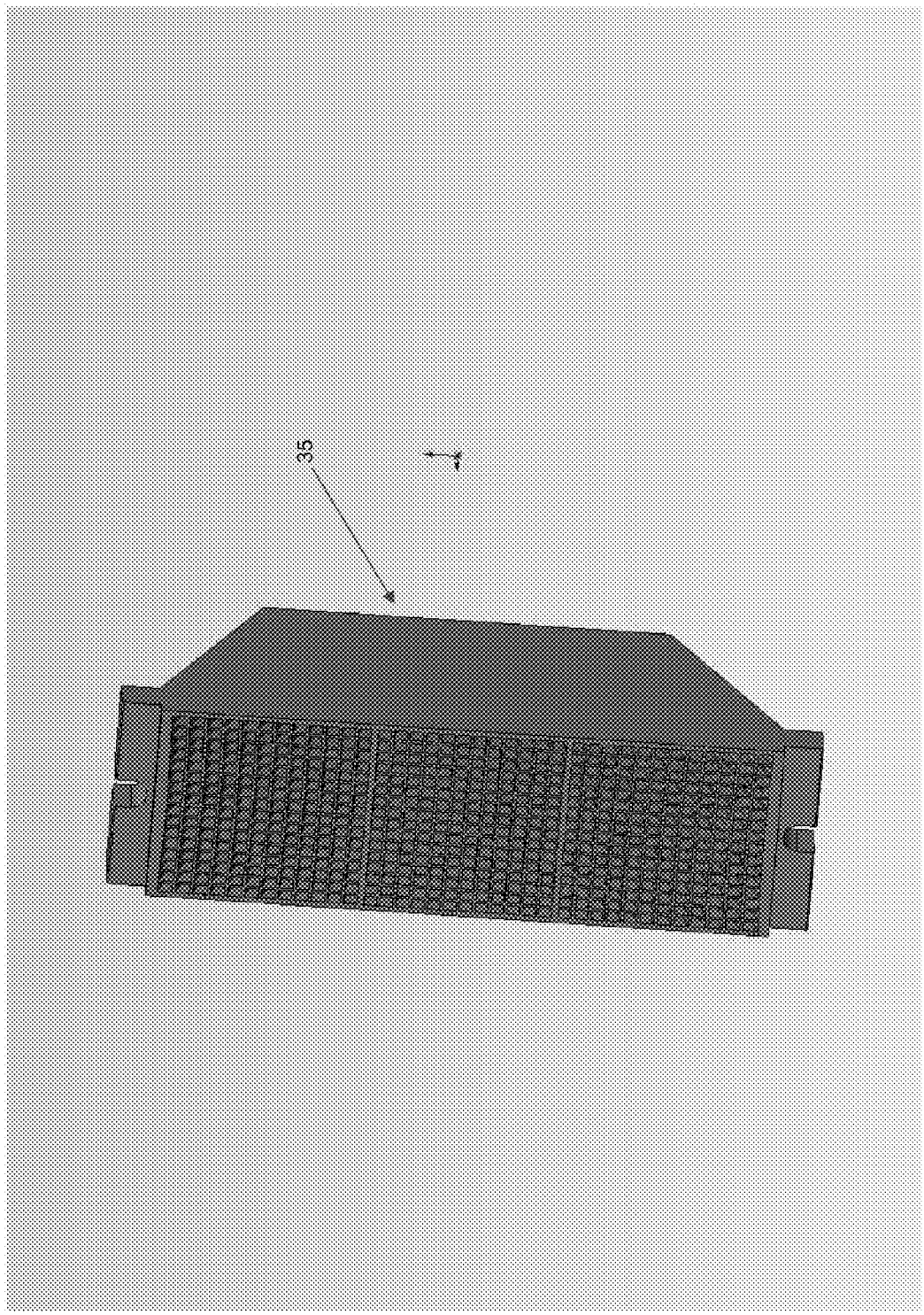
Figure 18:
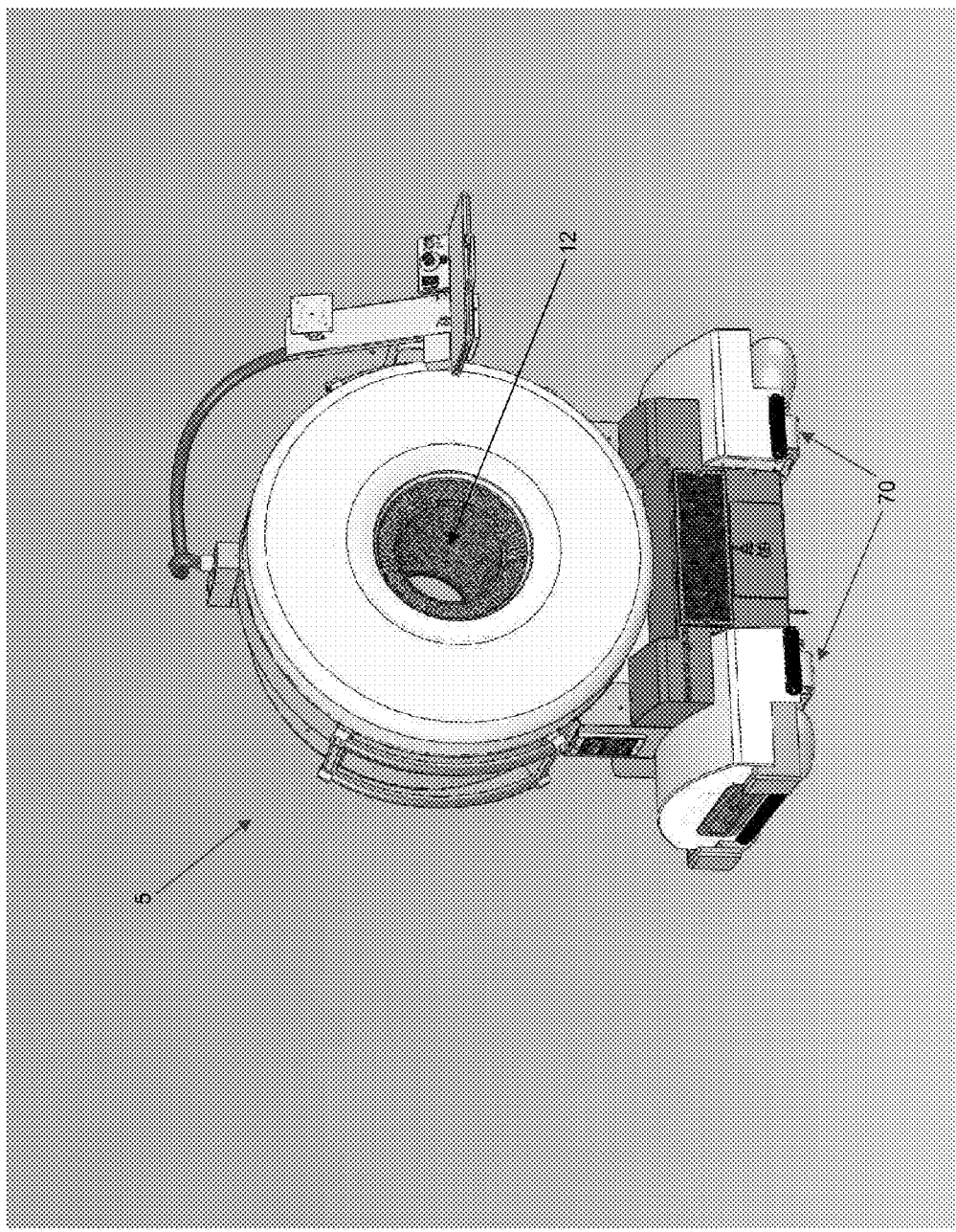
FIGS. 18-42 are schematic views showing selected aspects of a SPECT imaging system formed in accordance with the present invention, wherein the SPECT imaging system is adapted to move relative to the anatomy so as to produce volume scanning of the anatomy, e.g., in a manner analogous to that of the CT scanner disclosed in U.S. Pat. No. 7,175,347.
Figure 19:
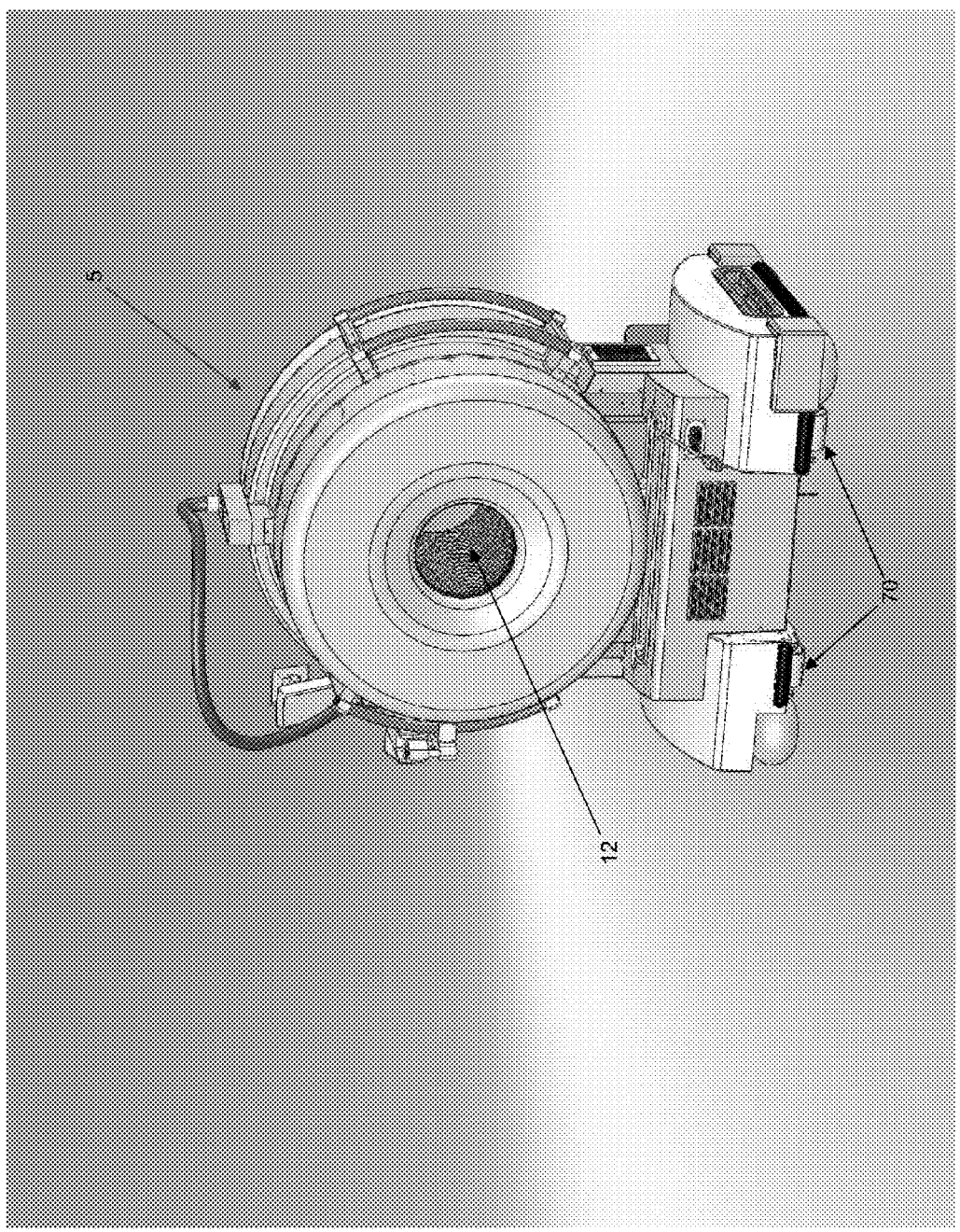
Figure 20:
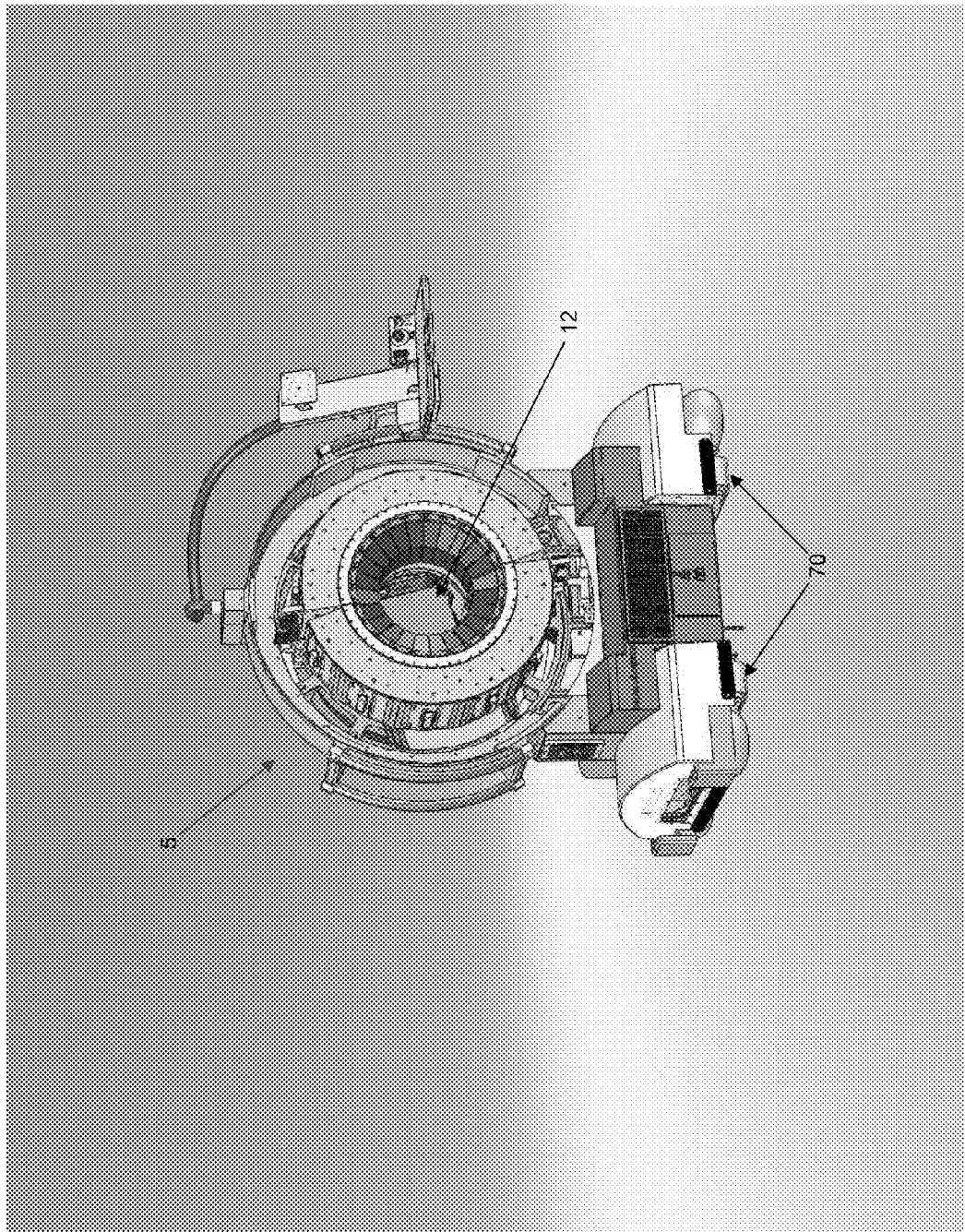
Figure 21:
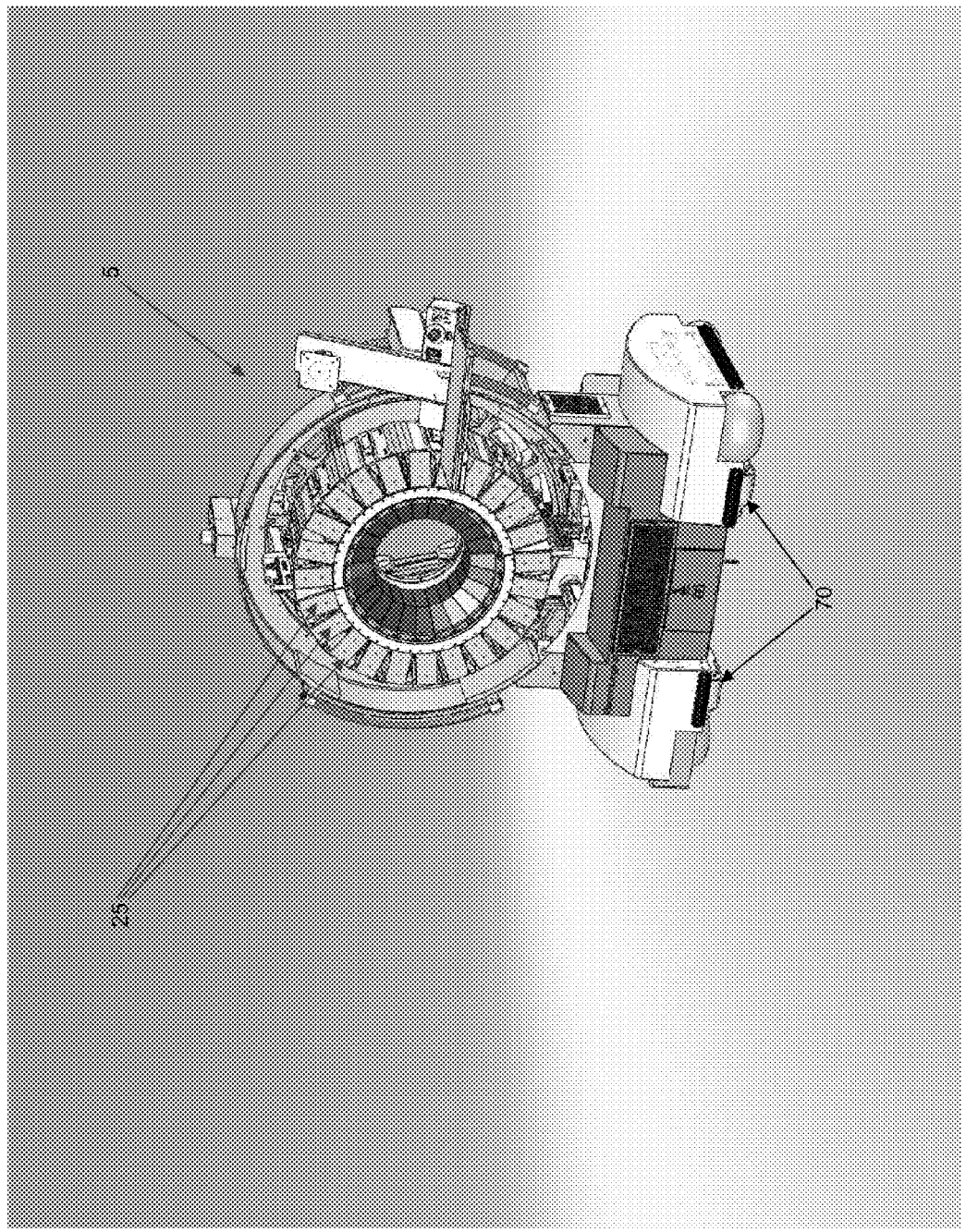
Figure 22:
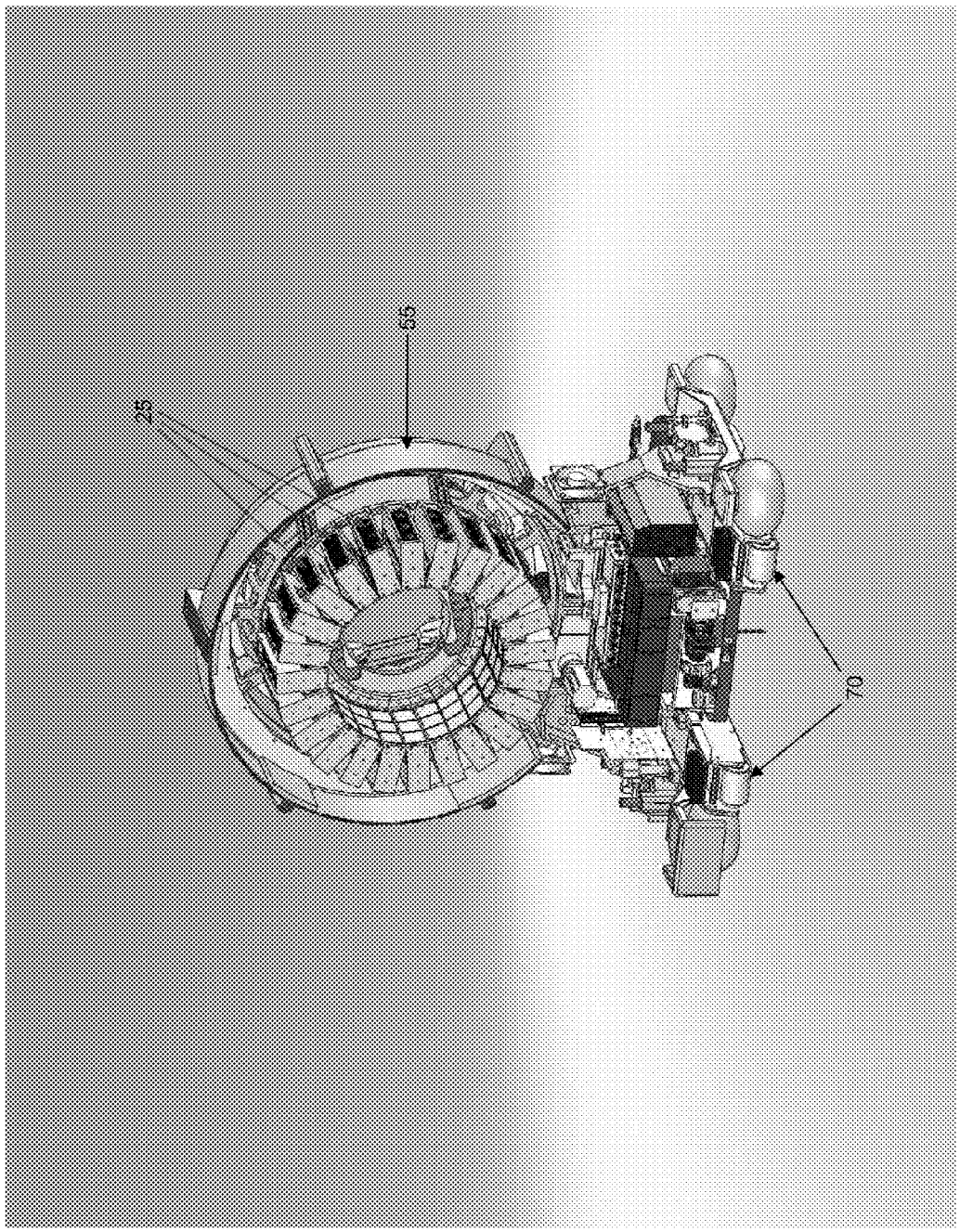
Figure 23:
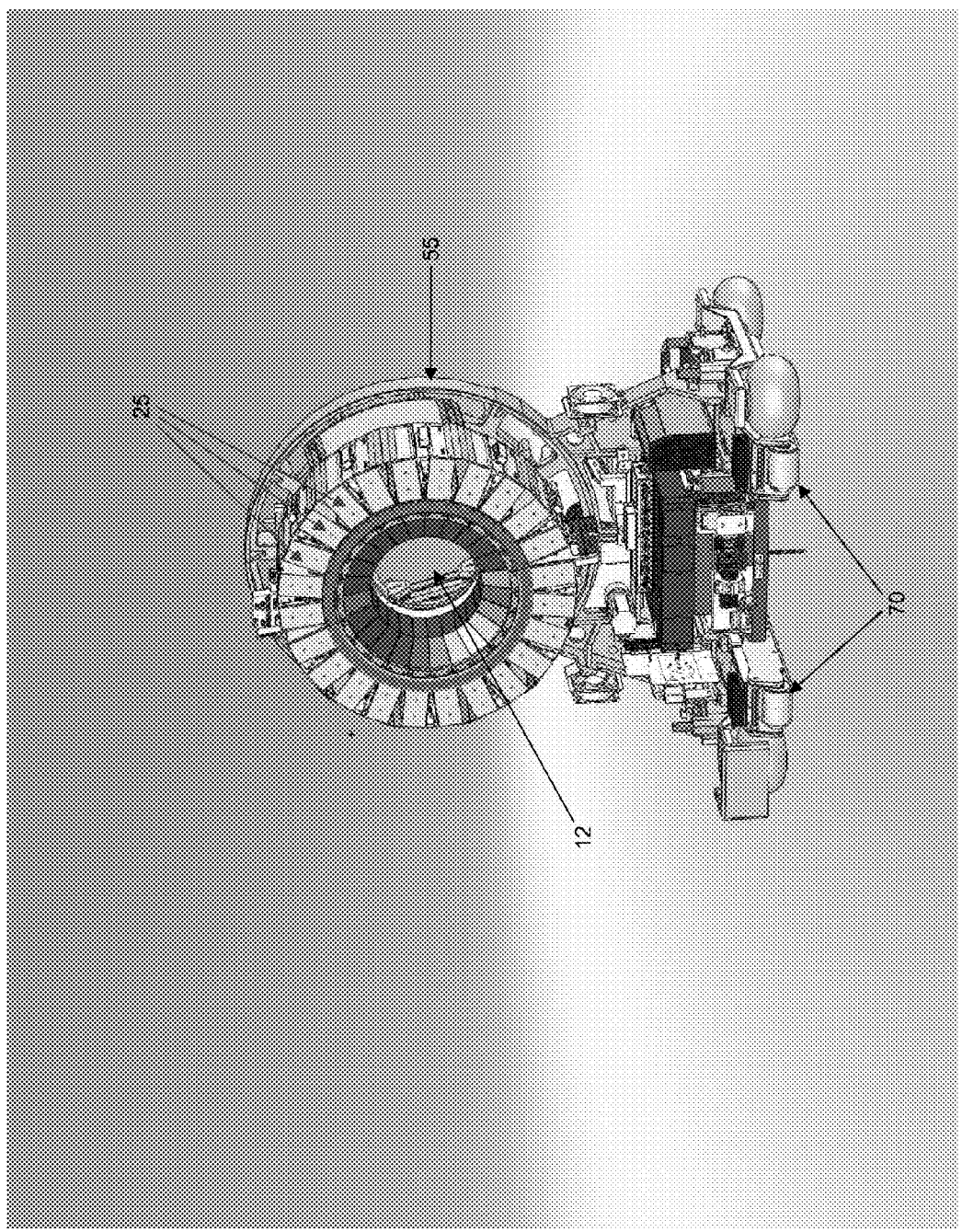
Figure 24:
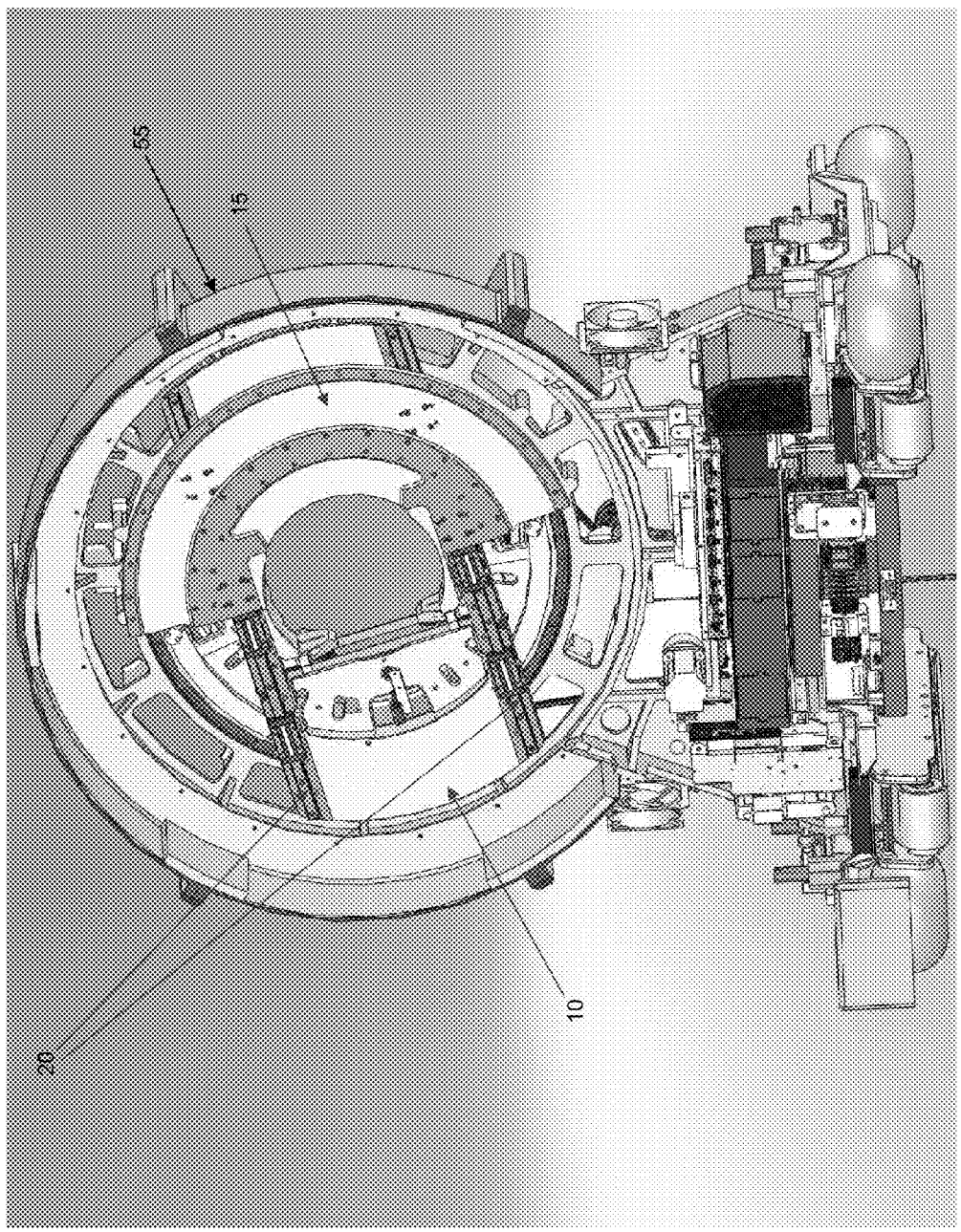
Figure 25:
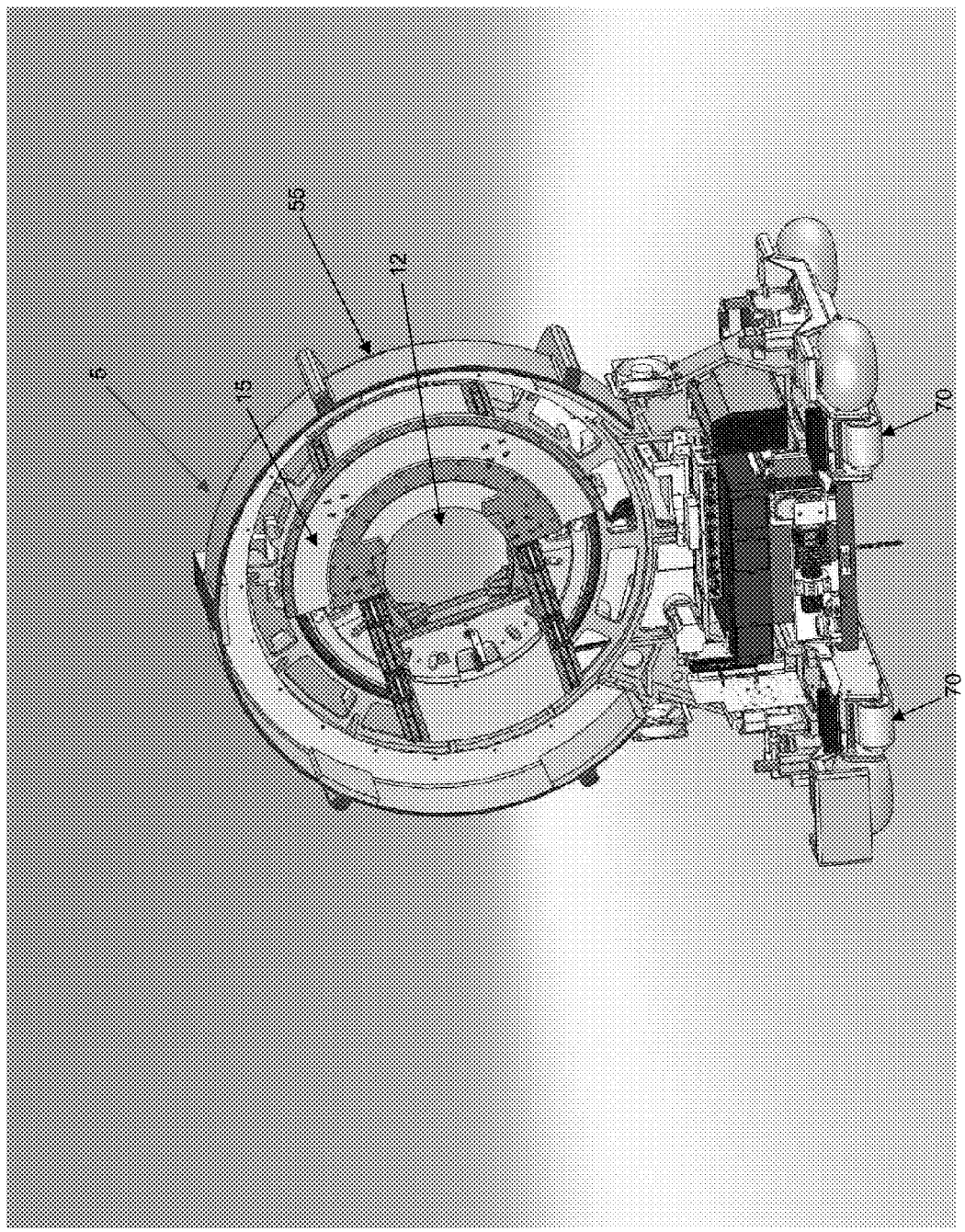
Figure 26:
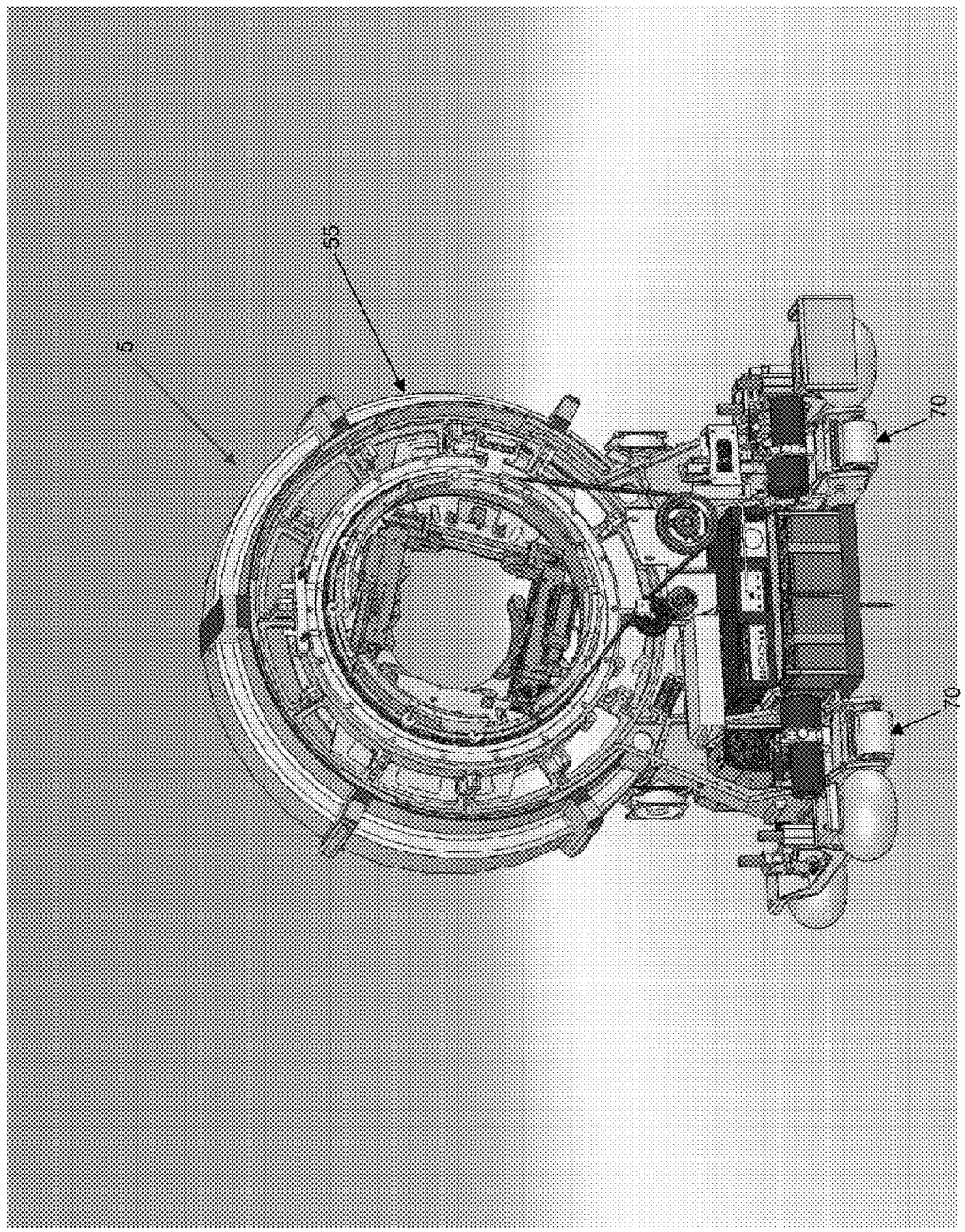
Figure 27:
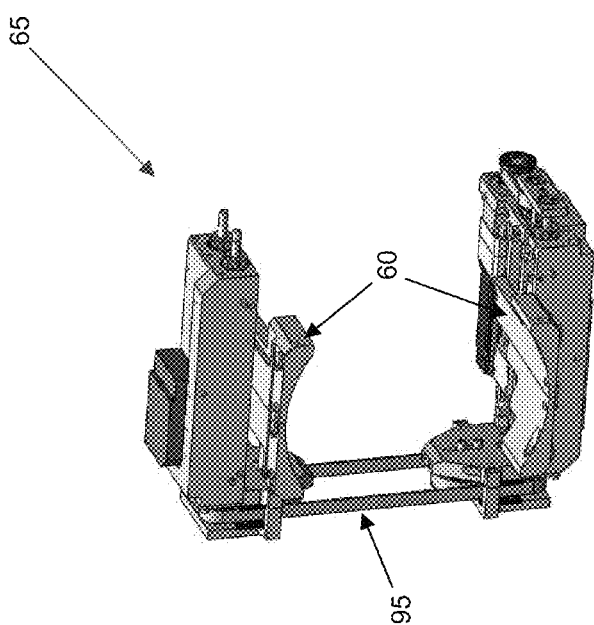
Figure 28:
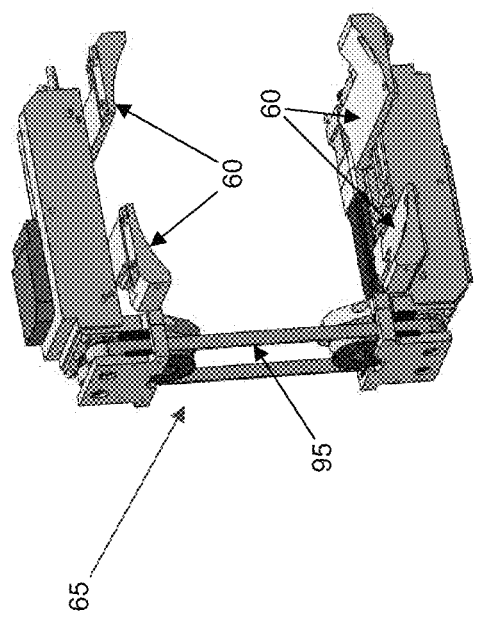
Figure 29:
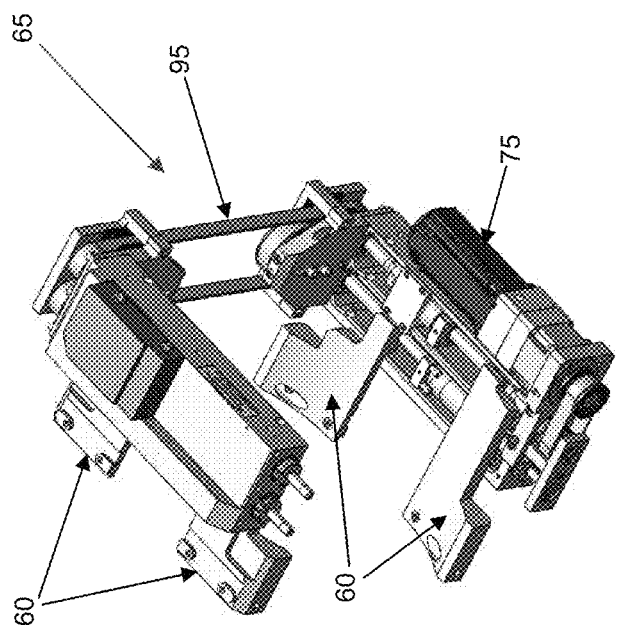
Figure 30:
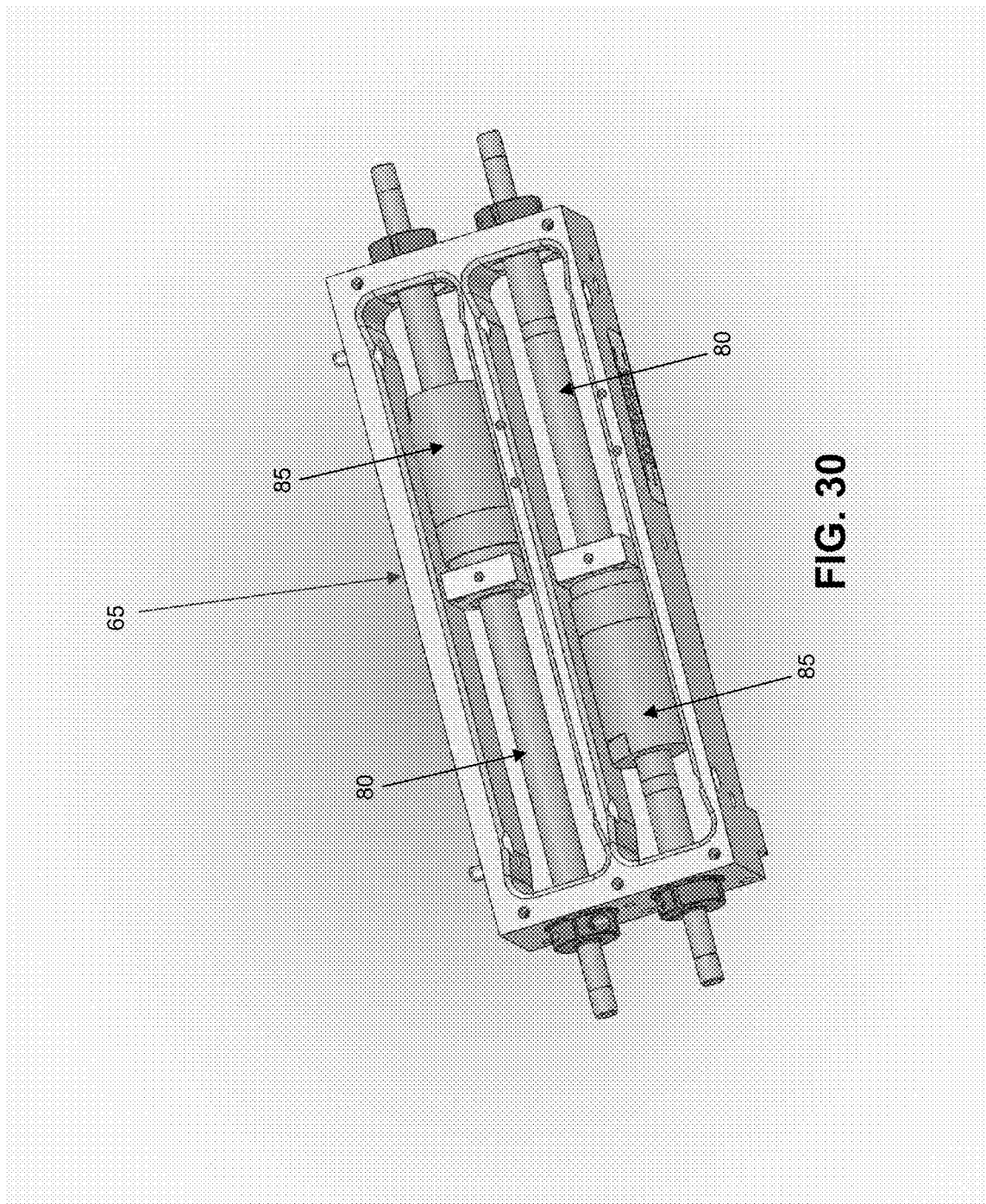
Figure 31:
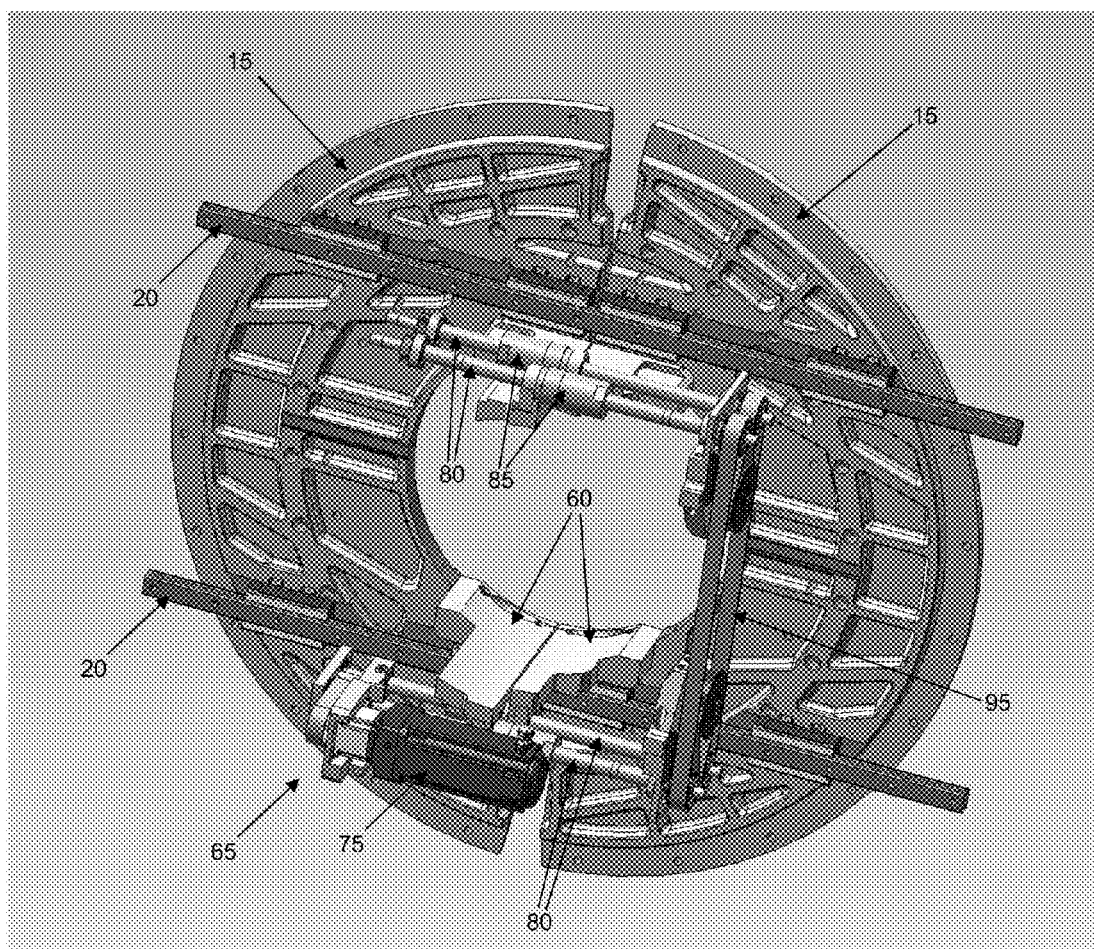
Figure 32:
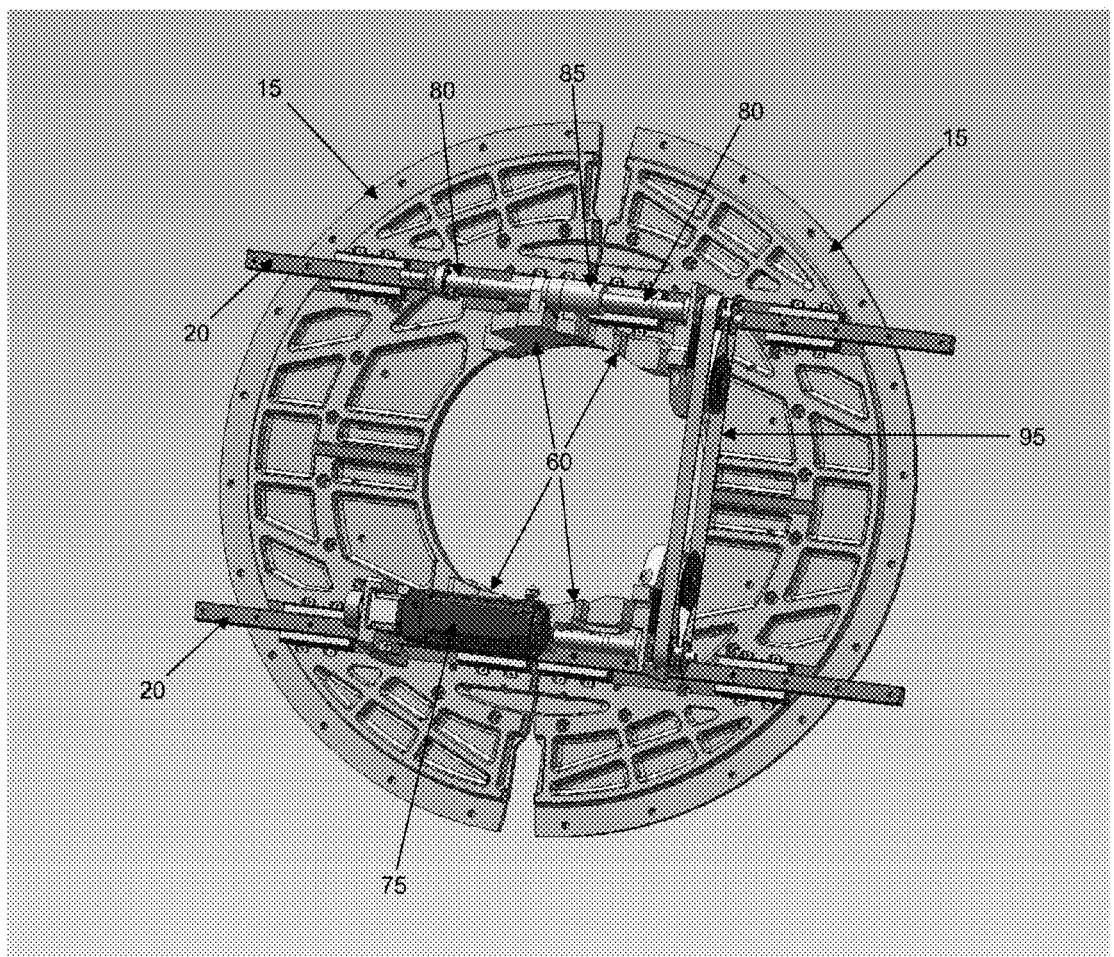
Figure 33:
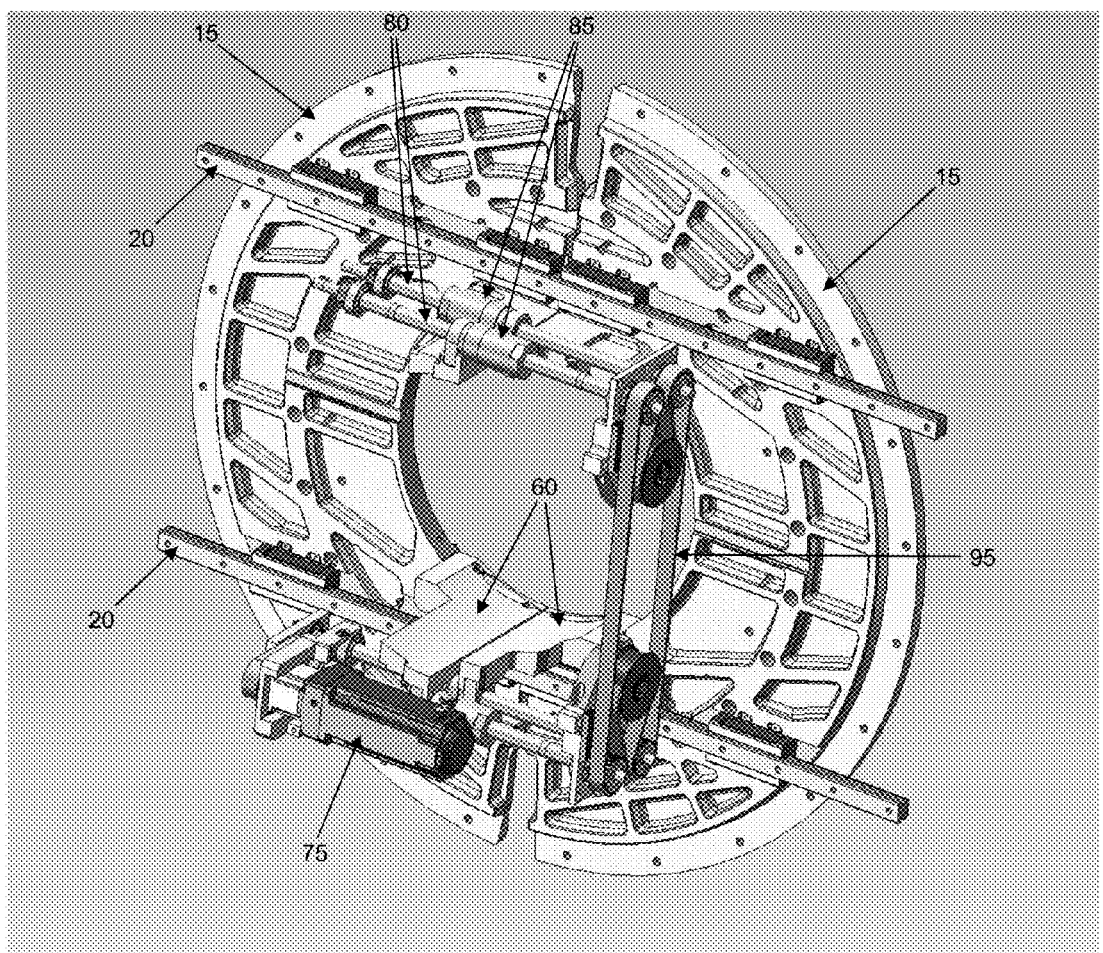
Figure 34:
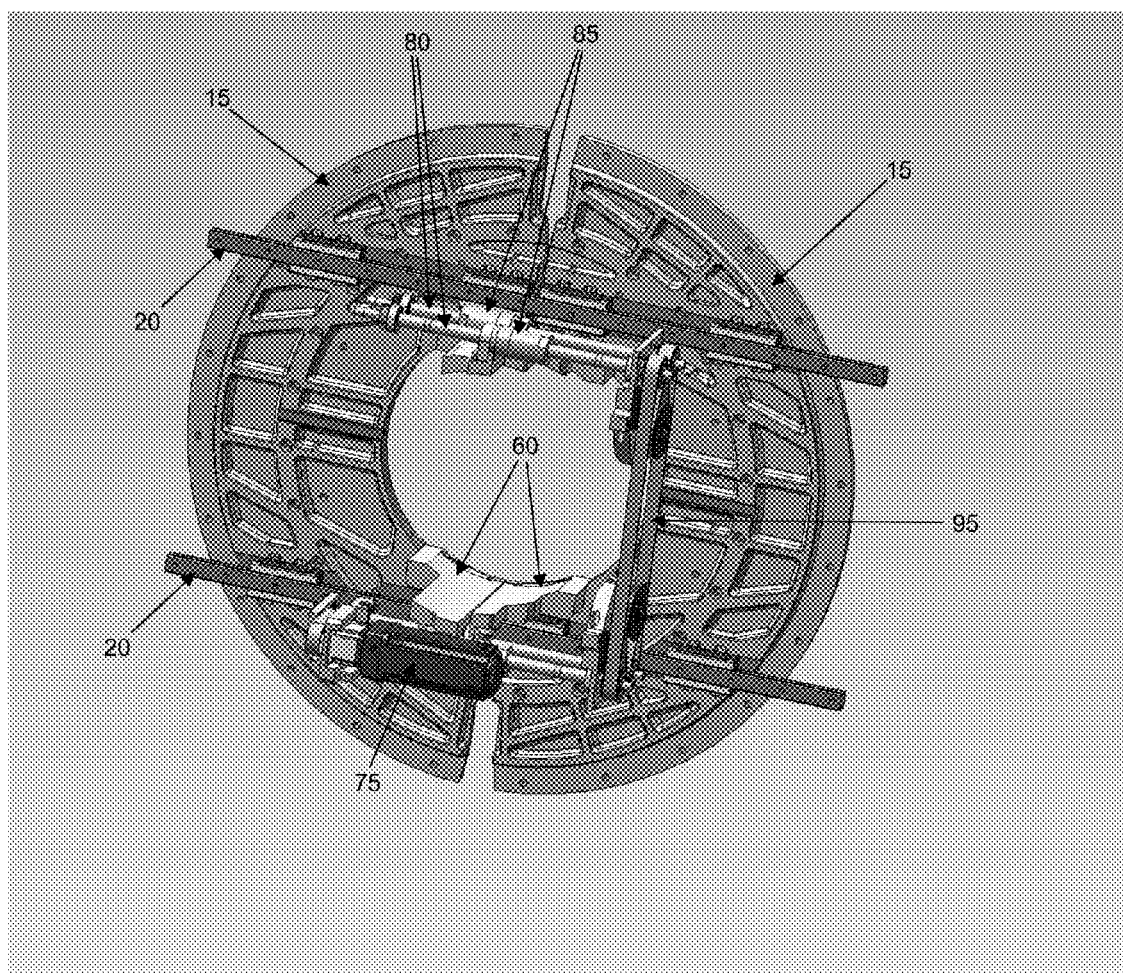
Figure 35:
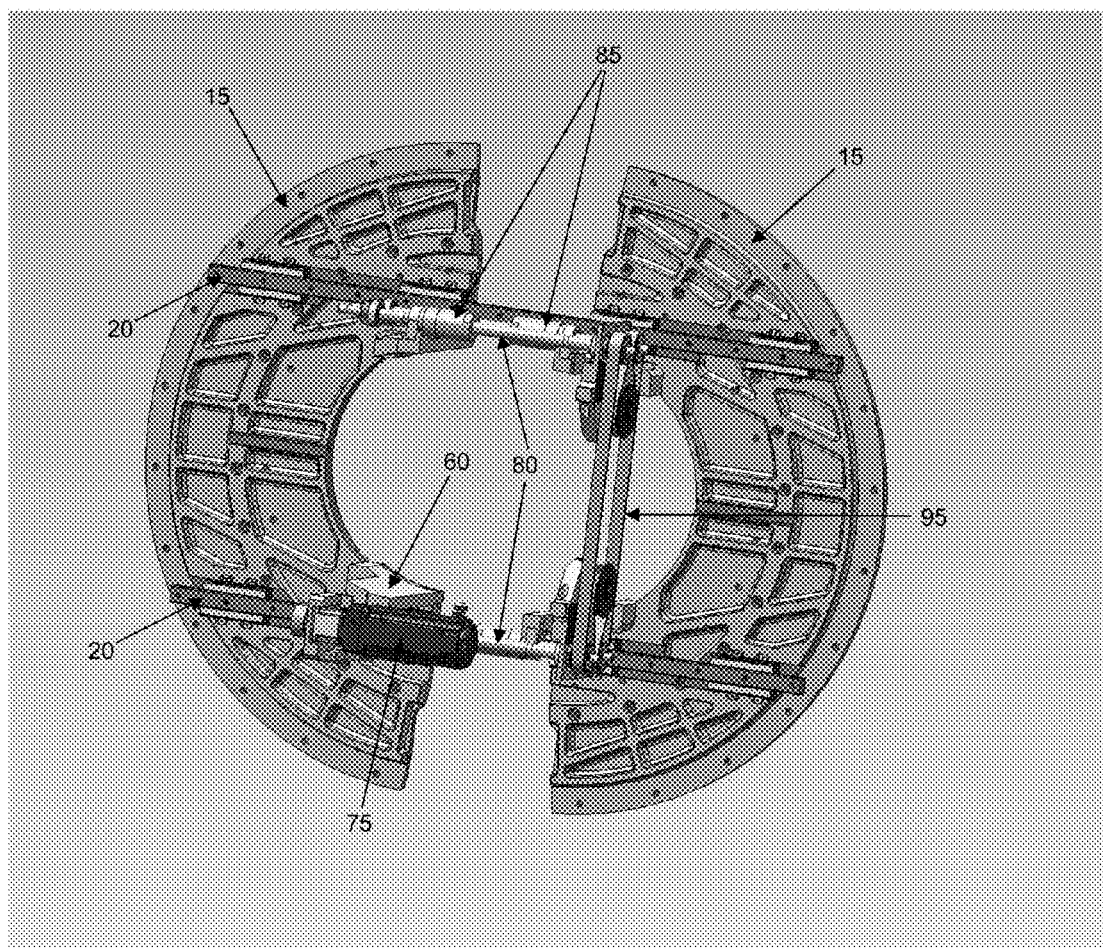
Figure 36:
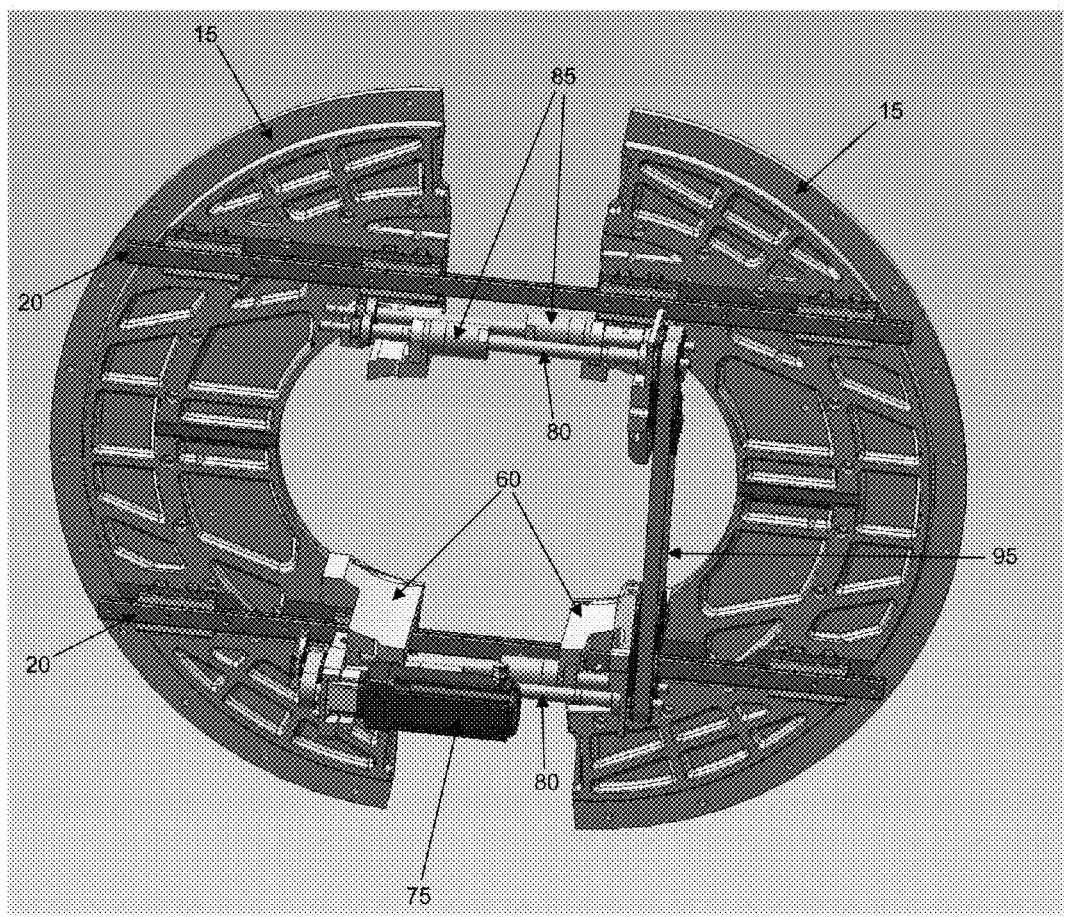
Figure 37:
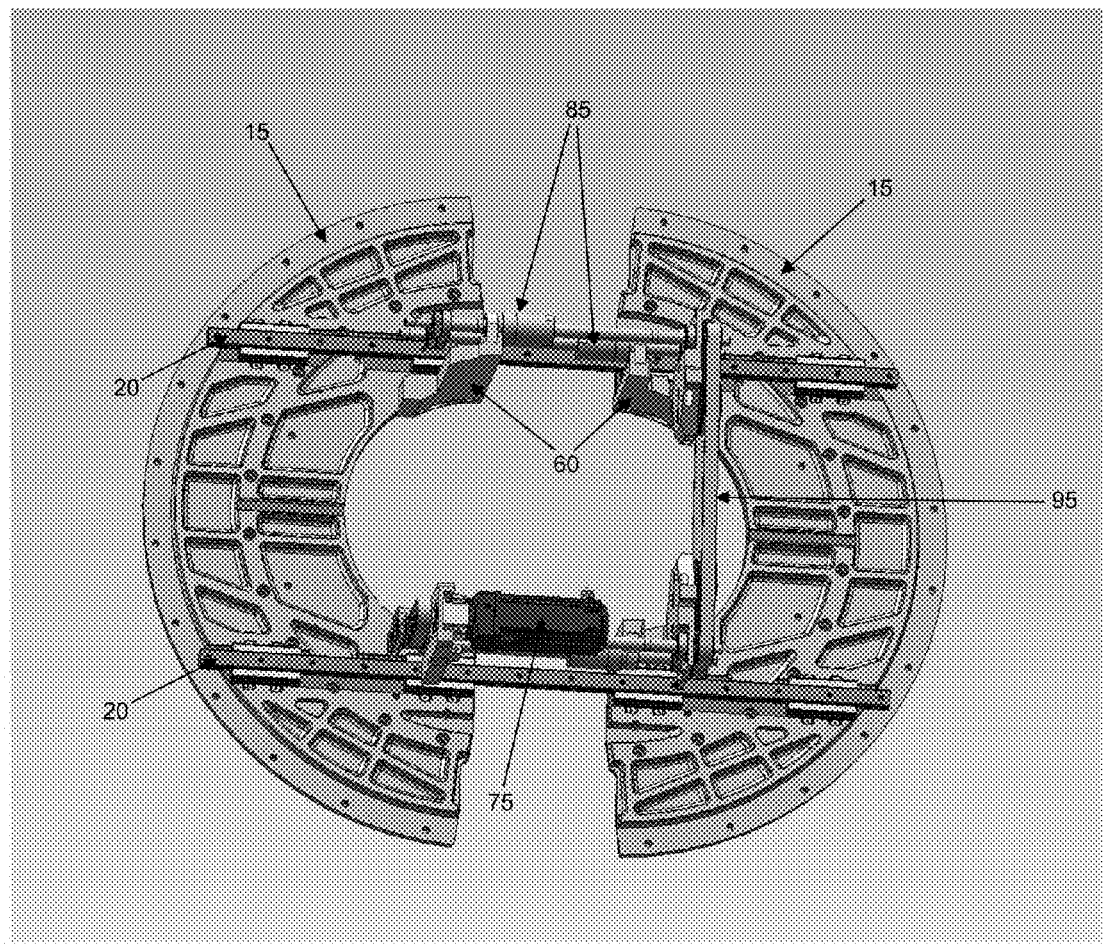
Figure 38:
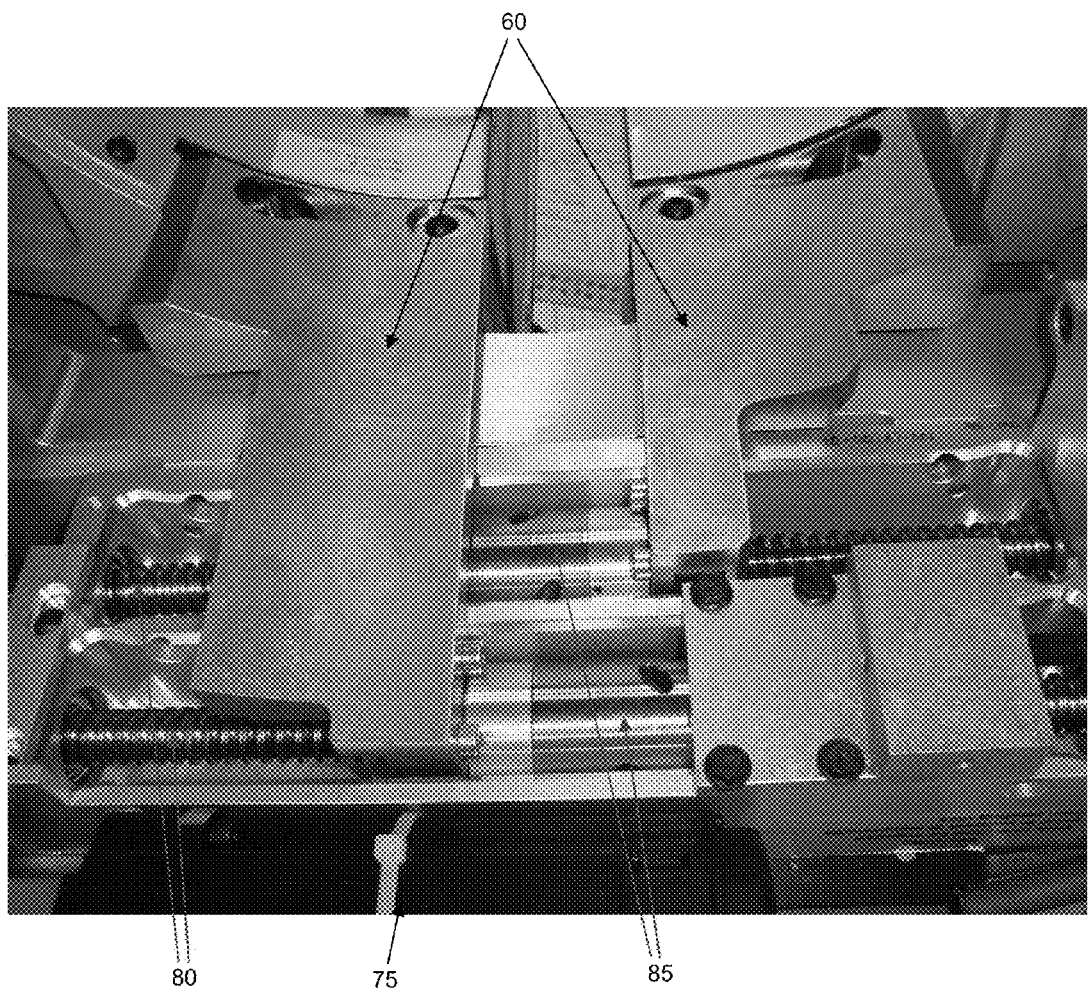
Figure 39:
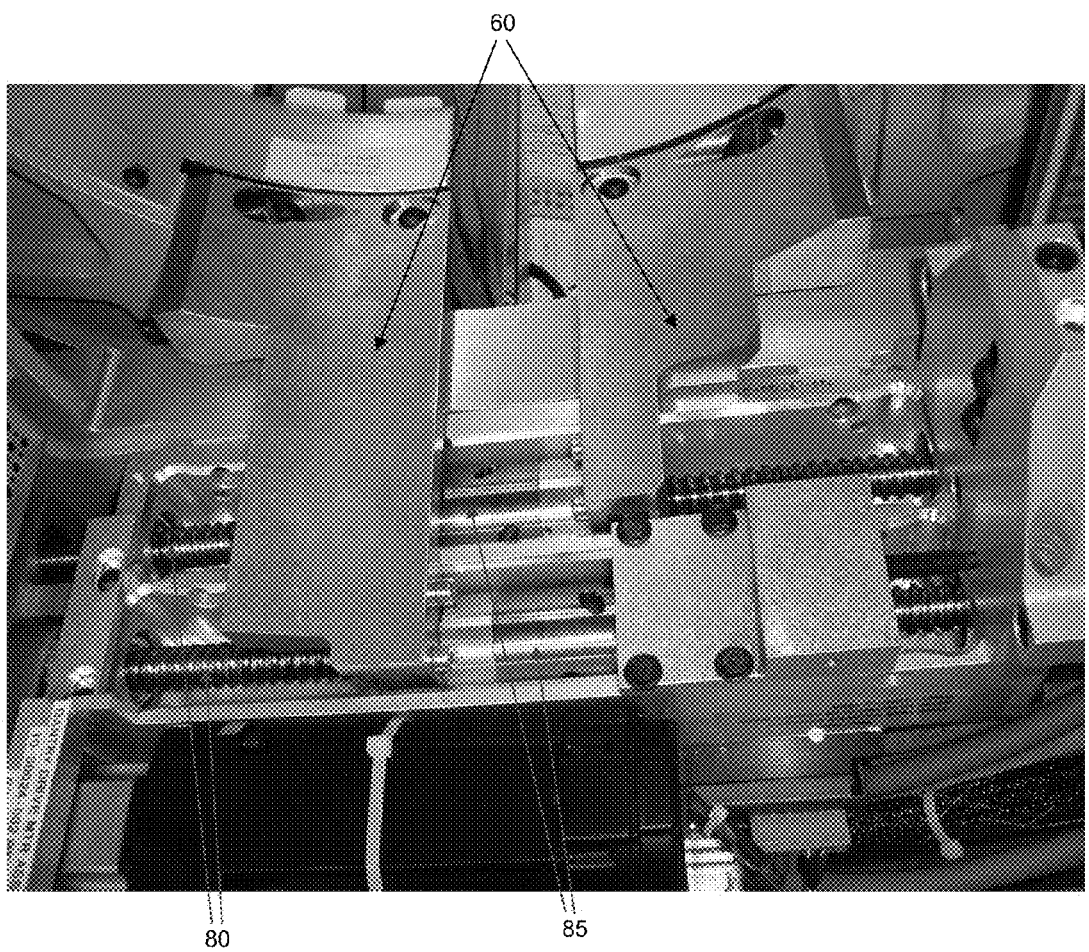
Figure 40:
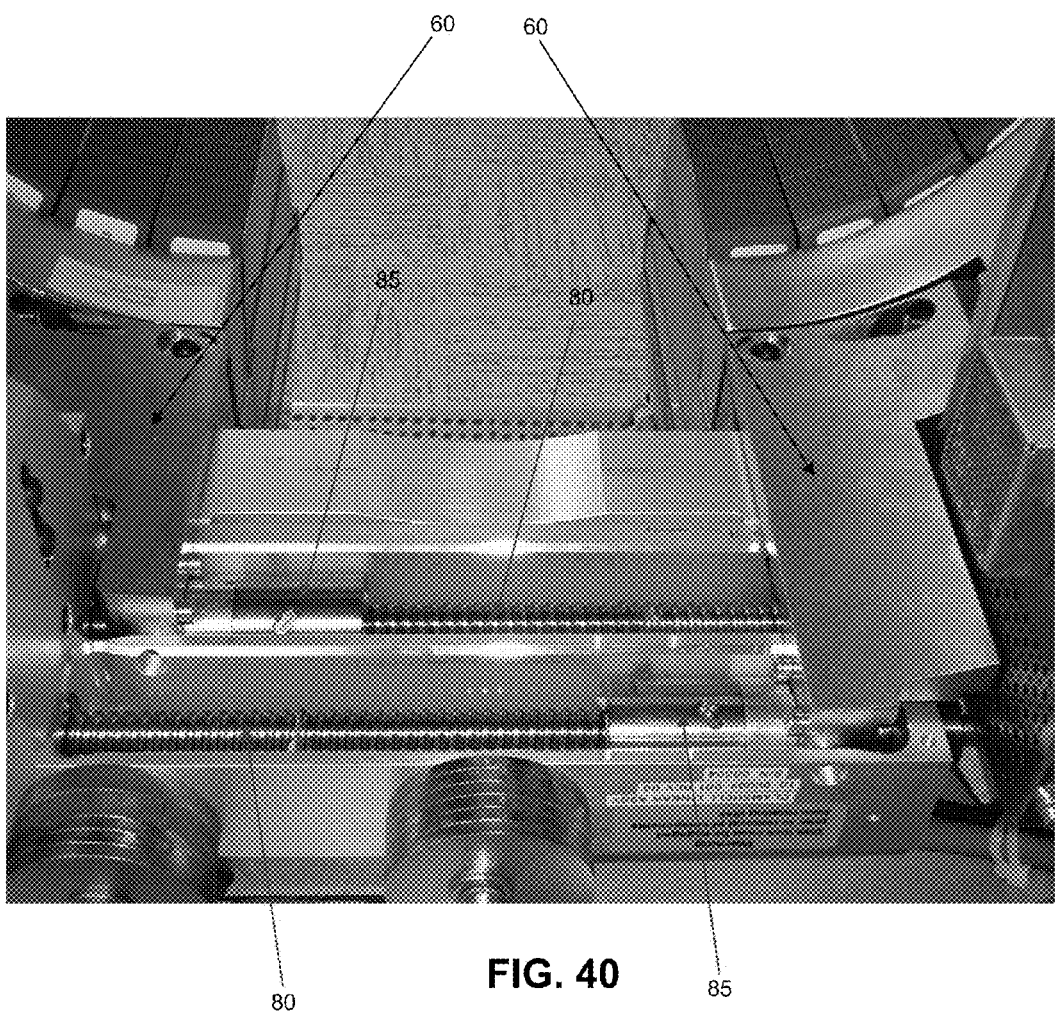
Figure 41:
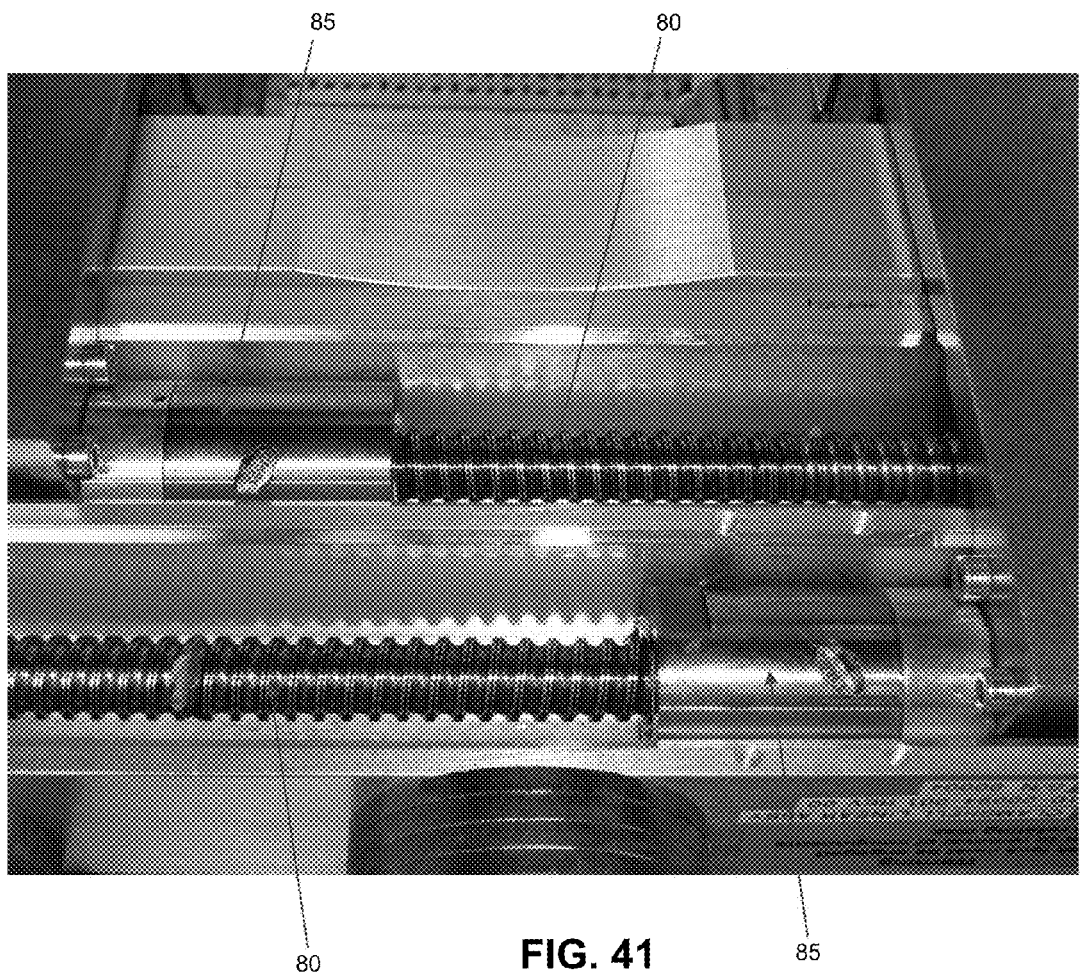
Figure 42:
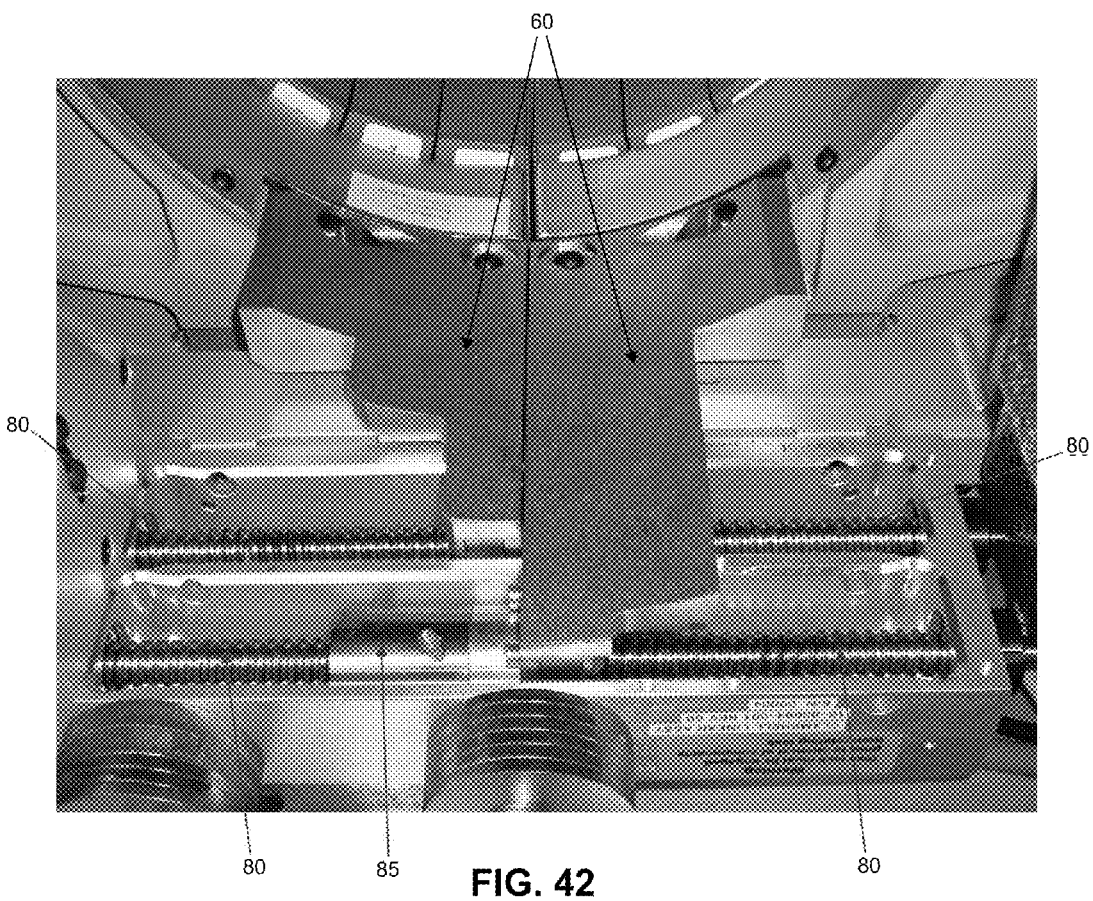

More particularly, and looking now at FIGS. 1-4, there is shown a novel SPECT system 5 formed in accordance with the present invention. Novel SPECT system 5 generally comprises a rotating ring 10 which surrounds the anatomy which is to be scanned. Rotating ring 10 includes a bore 12 for receiving the anatomy which is to be scanned. At least one camera mount 15 (e.g., 15A, 15B, etc.) is movably mounted to rotating ring 10 so that the camera mount can be moved radially relative to the rotating ring (i.e., so that the camera mount can be moved inwardly or outwardly relative to the axis of rotation of the rotating ring). By way of example but not limitation, the at least one camera mount 15 may be mounted to rails 20, which are in turn mounted to rotating ring 10, such that the at least one camera mount may move radially relative to rotating ring 10. The at least one camera mount carries a plurality of gamma cameras 25 (FIG. 4) thereon, with the plurality of gamma cameras 25 on that camera mount all being focused on a single SPECT focal point 30. More particularly, each of the gamma cameras comprises a collimator 35, and a scintillation crystal and associated electronics 40. The collimator is adapted to filter (or "focus") the field of radiation 45 emanating from the body of the patient, i.e., the radiation emanating from the SPECT focal point 30 to which that gamma camera is directed. The radiation passed by collimator 35 is then detected by scintillation crystal and associated electronics 40. As a result of the foregoing construction, as rotating ring 10 is rotated about the patient and camera mount 15 is moved radially on the rotating ring, the single SPECT focal point 30 of the gamma cameras 25 carried by that camera mount 15 follows a spiral path 50 through the anatomy. See FIG. 5. As a result, the anatomy traversed by the single SPECT focal point 50 is scanned by the SPECT imaging system so as to produce a scan of the anatomy.

While such scanning is occurring, the anatomy and/or the rotating ring 10 is/are preferably moved longitudinally relative to one another (i.e., along the axis of rotation of rotating ring 10), in the manner of a CT or MRI machine, so as to produce volume scanning of the anatomy. In this way, a 3D image of the patient's anatomy can be produced. By way of example but not limitation, the new SPECT imaging system may be adapted to move relative to the anatomy of the patient during scanning so as to produce volume scanning of the anatomy, e.g., in the manner of the moving CT scanner disclosed in U.S. Pat. No. 7,175,347, which patent is hereby incorporated herein by reference. Alternatively, the new SPECT imaging system may include a moving bed (not shown) which is adapted to move the anatomy of the patient relative to rotating ring 10 of the scanner during scanning so as to produce volume scanning of the anatomy.

In one preferred form of the invention, and as shown in FIGS. 1-4, two camera mounts 15A, 15B are provided on rotating ring 10, with the two camera mounts being disposed diametrically opposed to one another on the rotating ring. As noted above, each camera mount 15A, 15B carries a plurality of gamma cameras 25 thereon, with gamma cameras 25 being focused on SPECT focal points 30A, 30B, respectively. On account of this construction, two SPECT focal points 30A, 30B are provided, with each of the two SPECT focal points 30A, 30B following their own spiral patterns 50A, 50B through the anatomy, with the two SPECT focal points 30A, 30B being diametrically opposed to one another as they follow their respective spirals 50A, 50B through the anatomy. See FIG. 5. Preferably SPECT imaging system 5 is constructed so that the two SPECT focal points 30A, 30B can be superimposed on one another when their respective camera mounts 15A, 15B are appropriately positioned on rotating ring 10.

In another preferred form of the invention, just one camera mount 15 is provided on rotating ring 10, so that just one SPECT focal point 30 is provided.

And in another preferred form of the invention, three or more camera mounts 15 are provided, so that three or more SPECT focal points 30 are provided.

Looking next at FIGS. 6-17, there are shown selected aspects of a SPECT imaging system 5 formed in accordance with the present invention, wherein the SPECT imaging system 5 is adapted to move relative to the anatomy of the patient during scanning so as to produce volume scanning of the anatomy, e.g., in a manner analogous to that of the CT scanner disclosed in U.S. Pat. No. 7,175,347, which patent is hereby incorporated herein by reference. More particularly, in FIGS. 6-17, there is shown a frame 55 (FIG. 9) to which rotating ring 10 is mounted, and rails 20 which are mounted to rotating ring 10 and to which a pair of diametrically-opposed camera mounts 15A, 15B are mounted. Also shown is an exemplary gamma camera 25 (FIGS. 14 and 15) comprising its constituent collimator 35 (FIGS. 14-17) and its constituent scintillation crystal and associated electronics 40. Also shown are means for moving camera mounts 15A, 15B on rails 20, whereby to move camera mounts 15A, 15B in a radial manner relative to rotating ring 10. More particularly, in one preferred form of the invention, each of the camera mounts 15A, 15B has a lever 60 secured thereto. A drive unit 65 moves levers 60, whereby to move camera mounts 15 on rails 20 and hence to move camera mounts 15 radially relative to rotating ring 10. In addition to the foregoing, the SPECT imaging system 5 shown in FIGS. 6-17 also comprises centipede belt drives 70 for moving frame 55 relative to a patient who is disposed in bore 12, and hence moving rotating ring 10 (and hence camera mounts 15 and gamma cameras 25) relative to a patient who is disposed in bore 12.

FIGS. 18-42 show additional selected aspects of a SPECT imaging system 5 formed in accordance with the present invention. As seen in FIGS. 31-42, drive unit 65 comprises a motor 75 which drives a pair of screws 80. A ball nut 85 is mounted on each of the screws 80, such that rotation of screws 80 causes longitudinal motion of ball nuts 85 along screws 80. Note that screws 80 have threads 90 which turn in opposing directions, so that rotation of screws 80 in the same direction causes the pair of ball nuts 85 to move in opposing directions on their respective screws, i.e., either away from one another or towards one another. Levers 60 are mounted to ball nuts 85 and to camera mounts 15A, 15B. As a result of this construction, when motor 75 turns in one direction, ball nuts 85 are caused to move apart from one another, whereby to move camera mounts 15A, 15B apart from one another; and when motor 75 turns in the opposite direction, ball nuts 85 are caused to move toward one another, whereby to move camera mounts 15A, 15B toward one another. If desired, a belt 95 can be used to transfer rotary motion to a parallel screw/ball nut mechanism located on an opposing side of bore 12.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A high resolution single photon emission computed tomography (SPECT) imaging system comprising:

a rotating ring for surrounding anatomy which is to be imaged;

at least one camera mount movably mounted to the rotating ring so that the camera mount can be moved radially relative to the axis of rotation of the rotating ring; and at least one gamma camera carried on the at least one camera mount, wherein the at least one gamma camera is focused on a single SPECT focal point;

whereby, when the rotating ring is rotated about the anatomy which is to be imaged and the at least one camera mount is moved radially on the rotating ring, the single SPECT focal point of the at least one gamma camera carried by a camera mount follows a spiral pattern through the anatomy, whereby to produce a scan of the anatomy;

wherein a plurality of camera mounts are movably mounted on the rotating ring so that each camera mount can be moved radially relative to the axis of rotation of the rotating ring, and further wherein each of the plurality of camera mounts comprises at least one gamma camera focused on a single SPECT focal point for that camera mount; and wherein two camera mounts are provided on the rotating ring, with the two camera mounts being disposed diametrically opposed to one another on the rotating ring, such that two SPECT focal points are provided, with each of the two SPECT focal points following a spiral pattern through the anatomy as the rotating ring is rotated about the anatomy which is to be imaged and two camera mounts are moved radially on the rotating ring, with the two SPECT focal points being diametrically opposed to one another as they follow their respective spiral paths.

2. The high resolution single photon emission computed tomography (SPECT) imaging system according to claim 1 wherein at least one of the anatomy and the rotating ring is moved longitudinally relative to the other during scanning, whereby to produce a volume scan of the anatomy.

3. The high resolution single photon emission computed tomography (SPECT) imaging system according to claim 2 wherein the rotating ring is moved longitudinally relative to the patient.

4. The high resolution single photon emission computed tomography (SPECT) imaging system according to claim 3 wherein the rotating ring is mounted to a frame, and further wherein the frame is moved along a surface using a continuous loop drive.

5. The high resolution single photon emission computed tomography (SPECT) imaging system according to claim 4 wherein the continuous loop drive comprises a pair of centipede belt drives.

6. The high resolution single photon emission computed tomography (SPECT) imaging system according to claim 2 wherein the patient is moved longitudinally relative to the rotating ring.

7. The high resolution single photon emission computed tomography (SPECT) imaging system according to claim 6 wherein the patient is moved relative to the rotating ring using a motorized bed.

8. The high resolution single photon emission computed tomography (SPECT) imaging system according to claim 1 wherein the at least one gamma camera carried on each of the camera mounts comprises a collimator and a scintillation crystal and associated electronics.

9. The high resolution single photon emission computed tomography (SPECT) imaging system according to claim 1 wherein a plurality of gamma cameras are carried on each of the camera mounts, with the plurality of gamma cameras on a given camera mount all being focused on a single SPECT focal point for that camera mount.

10. The high resolution single photon emission computed tomography (SPECT) imaging system according to claim 1 wherein the two SPECT focal points can be superimposed on one another when their respective camera mounts are appropriately positioned on the rotating ring.

11. The high resolution single photon emission computed tomography (SPECT) imaging system according to claim 1 wherein each of the camera mounts are moved relative to the rotating ring using a rotating screw and a ball nut fixed to each of the camera mounts and riding on the rotating screw.

12. A method for imaging anatomy, the method comprising:
providing a high resolution single photon emission computed tomography (SPECT) imaging system comprising:
a rotating ring for surrounding anatomy which is to be imaged;
at least one camera mount movably mounted to the rotating ring so that the camera mount can be moved radially relative to the axis of rotation of the rotating ring; and
at least one gamma camera carried on the at least one camera mount, wherein the at least one gamma camera is focused on a single SPECT focal point;
wherein a plurality of camera mounts are movably mounted on the rotating ring so that each camera mount can be moved radially relative to the axis of rotation of the rotating ring, and further wherein each of the plurality of camera mounts comprises at least one gamma camera focused on a single SPECT focal point for that camera mount; and
wherein two camera mounts are provided on the rotating ring, with the two camera mounts being disposed diametrically opposed to one another on the rotating ring, such that two SPECT focal points are provided; and
rotating the rotating ring about the anatomy which is to be imaged and moving each of the two camera mounts radially on the rotating ring, so that each of the two SPECT focal points follows a spiral pattern through the anatomy, with the two SPECT focal points being diametrically opposed to one another as they follow their respective spiral paths, whereby to produce a scan of the anatomy.

13. The method according to claim 12 wherein at least one of the anatomy and the rotating ring is moved longitudinally relative to the other during scanning, whereby to produce a volume scan of the anatomy.

14. The method according to claim 13 wherein the rotating ring is moved longitudinally relative to the patient.

15. The method according to claim 14 wherein the rotating ring is mounted to a frame, and further wherein the frame is moved along a surface using a continuous loop drive.

16. The method according to claim 15 wherein the continuous loop drive comprises a pair of centipede belt drives.

17. The method according to claim 13 wherein the patient is moved longitudinally relative to the rotating ring.

18. The method according to claim 17 wherein the patient is moved relative to the rotating ring using a motorized bed.

19. The method according to claim 12 wherein the at least one gamma camera carried on each of the camera mounts comprises a collimator and a scintillation crystal and associated electronics.

20. A method according to claim 12 wherein a plurality of gamma cameras are carried on each of the camera mounts, with the plurality of gamma cameras on a given camera mount all being focused on a single SPECT focal point for that camera mount.

21. The method according to claim 12 wherein the two SPECT focal points can be superimposed on one another when their respective camera mounts are appropriately positioned on the rotating ring.

22. A method for imaging anatomy, the method comprising:
providing two cameras focused on two focal points, with the two cameras being disposed diametrically opposed to one another; and
simultaneously moving, circumferentially and radially, each of the two cameras relative to the anatomy so that the two focal points follow a spiral pattern through the anatomy, with the two focal points being diametrically opposed to one another as they follow their respective spiral paths, whereby to produce a scan of the anatomy.

* * * * *